United States Patent
Park et al.

(10) Patent No.: US 10,543,258 B2
(45) Date of Patent: *Jan. 28, 2020

(54) ANTIBACTERIAL COMPOSITION CONTAINING ADK PROTEIN AS ACTIVE INGREDIENT, OR COMPOSITION FOR PREVENTING OR TREATING SEPSIS

(71) Applicant: KONKUK UNIVERSITY GLOCAL INDUSTRY-ACADEMIC COLLABORATION FOUNDATION, Chungju-si, Chungcheongbuk-do (KR)

(72) Inventors: Yeong Min Park, Seoul (KR); In Duk Jung, Cheongju-si (KR); Yong Taik Lim, Seongnam-si (KR); Jung Hee Park, Iksan-si (KR); Sung Jae Shin, Seoul (KR)

(73) Assignee: KONKUK UNIVERSITY GLOCAL INDUSTRY-ACADEMIC COLLABORATION FOUNDATION, Chungju-si, Chungcheon (KR)

( * ) Notice: Subject to any disclaimer, the term of this patent is extended or adjusted under 35 U.S.C. 154(b) by 207 days.

This patent is subject to a terminal disclaimer.

(21) Appl. No.: 15/534,979

(22) PCT Filed: Dec. 10, 2015

(86) PCT No.: PCT/KR2015/013521
§ 371 (c)(1),
(2) Date: Jun. 9, 2017

(87) PCT Pub. No.: WO2016/093641
PCT Pub. Date: Jun. 16, 2016

(65) Prior Publication Data
US 2019/0083581 A1   Mar. 21, 2019

(30) Foreign Application Priority Data
Dec. 10, 2014   (KR) .................. 10-2014-0177329
Dec. 10, 2014   (KR) .................. 10-2014-0177352

(51) Int. Cl.
| | |
|---|---|
| *A61K 38/00* | (2006.01) |
| *A61K 38/45* | (2006.01) |
| *A61P 31/04* | (2006.01) |
| *A61K 31/345* | (2006.01) |
| *A61K 31/43* | (2006.01) |
| *A61K 31/47* | (2006.01) |
| *A61K 31/545* | (2006.01) |
| *A61K 31/65* | (2006.01) |
| *A61K 31/7036* | (2006.01) |
| *C12N 9/12* | (2006.01) |

(52) U.S. Cl.
CPC ............ *A61K 38/45* (2013.01); *A61K 31/345* (2013.01); *A61K 31/43* (2013.01); *A61K 31/47* (2013.01); *A61K 31/545* (2013.01); *A61K 31/65* (2013.01); *A61K 31/7036* (2013.01); *A61P 31/04* (2018.01); *C12N 9/1229* (2013.01); *C12Y 207/04003* (2013.01)

(58) Field of Classification Search
None
See application file for complete search history.

(56) References Cited

FOREIGN PATENT DOCUMENTS

| KR | 10-1182582 | 9/2012 |
| KR | 10-1477795 | 1/2015 |

OTHER PUBLICATIONS

Cloning and Sequencing of *Mycobacterium bovis* BCG gene cluster containing secY Biochem. Mol. Biol. Int. 43 (2), 391-398, 1997.*
Lee et al; "Protective Efficacy of Recombinant Proteins Adenylate Kinase, Nucleoside Diphosphate Kinase, and Heat-Shock Protein 70 against *Mycobacterium tuberculosis* Infection in Mice", Tuberculosis and Respiratory Diseases, vol. 58, No. 2, pp. 142-152 (2005).
Lee et al; "Investigation of the Growth Rate Change in Recombinant BCG which was cloned *Mycobacterium tuberculosis* Adenylate Kinase Mutation Gene or Human Muscle-type Adenylate Kinase Synthetic Gene", Tuberculosis and Respiratory Diseases, vol. 60, No. 2, pp. 187-193 (2006).
NCBI Reference Sequence No. WP_003403726.1 (Aug. 29, 2013), available at http://www.ncbi.nlm.nih.gov/protein/489498816?sat=45570783.
NCBI GenBank accession No. U77912.1 (Jan. 27, 1999), available at http://www.ncbi.nlm.nih.gov/nuccore/u77912.1.

* cited by examiner

*Primary Examiner* — Jeanette M Lieb
(74) *Attorney, Agent, or Firm* — Vorys, Sater, Seymour & Pease LLP; Mih Suhn Koh

(57) ABSTRACT

The present invention relates to an antibacterial composition containing, as an active ingredient, adenylate kinase or adenosine kinase (ADK) protein derived from *Mycobacterium tuberculosis*, and a composition for preventing or treating infectious diseases. In addition, the present invention relates to a composition for preventing or treating sepsis or septic shock. Furthermore, the present invention relates to a method for preventing, improving or treating an infectious disease comprising administering the present antibacterial composition. The ADK protein derived from *Mycobacterium tuberculosis* according to the present invention has excellent antibacterial activity selectively against gram-negative bacteria, and thus can be favorably used as an antibacterial composition against gram-negative bacteria or for the prevention or treatment of infectious diseases caused by gram-negative bacteria. In addition, the ADK protein has an excellent sepsis treatment effects, thus can be favorably used for the prevention or treatment of sepsis or septic shock.

14 Claims, 14 Drawing Sheets

Specification includes a Sequence Listing.

FIG. 6
*E.coli*/AnNPs control
*E.coli*/AnNPs-Adk
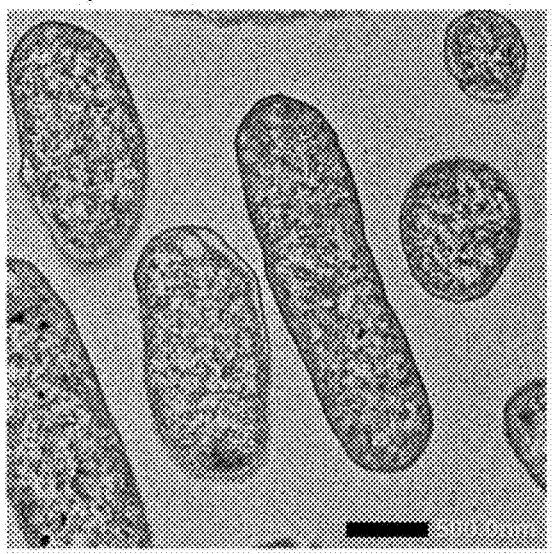
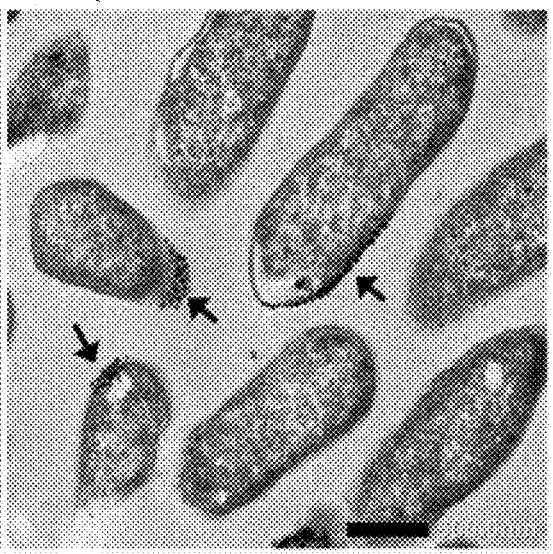

FIG. 7
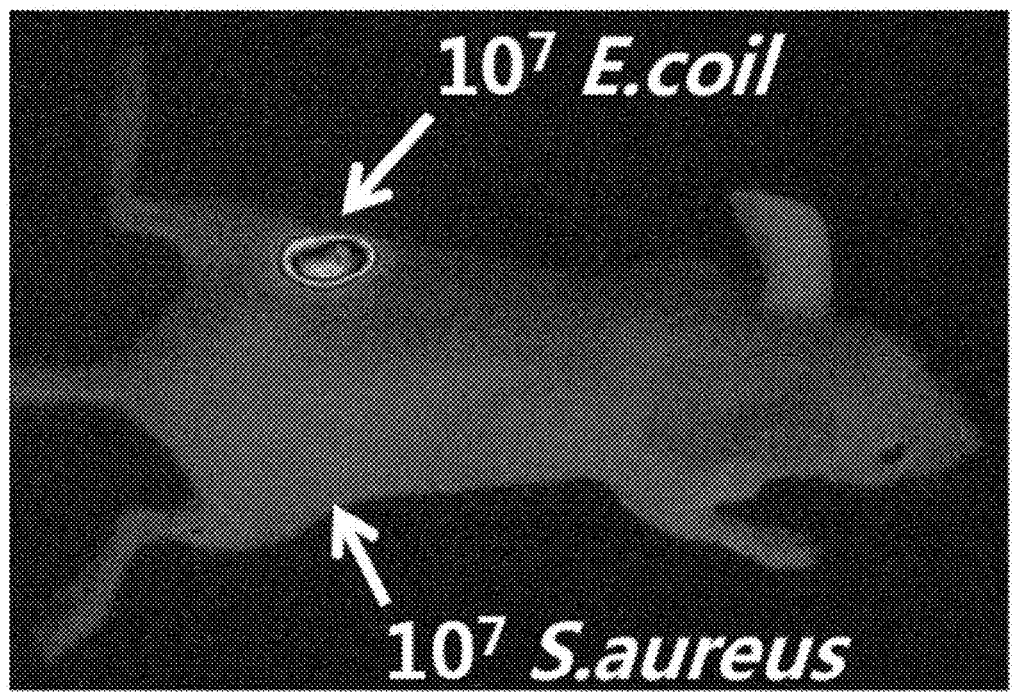
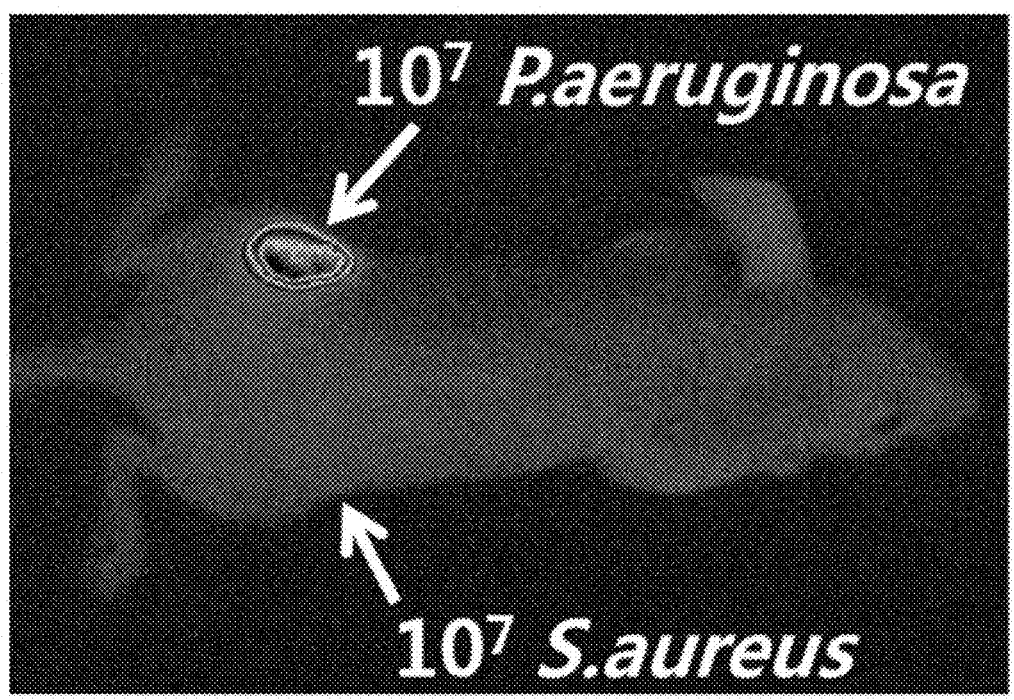

FIG. 8
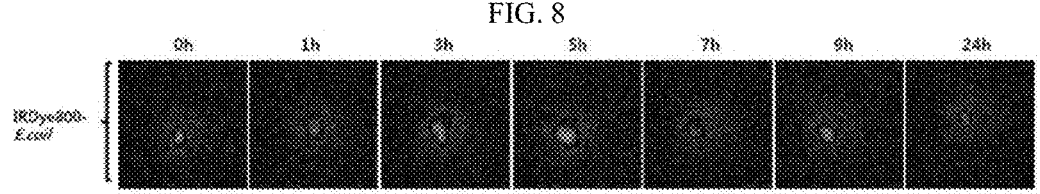
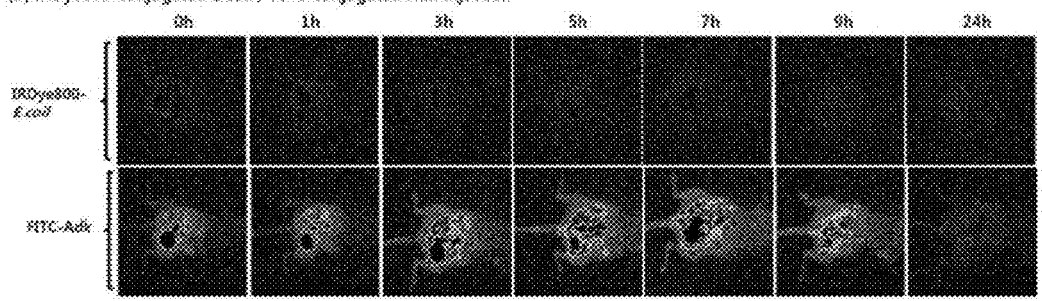
FIG. 9
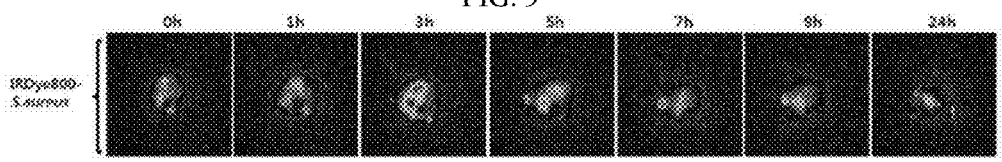
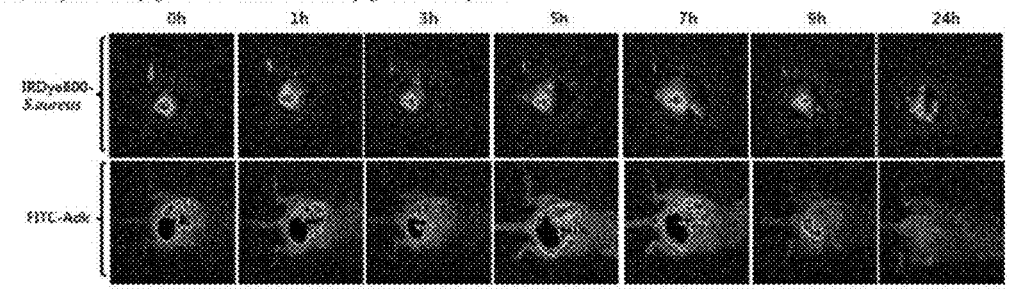

ANTIBACTERIAL COMPOSITION CONTAINING ADK PROTEIN AS ACTIVE INGREDIENT, OR COMPOSITION FOR PREVENTING OR TREATING SEPSIS

STATEMENT REGARDING GOVERNMENT RIGHTS

The present invention was undertaken with the support of 1) the National Research Foundation of Korea (NRF) No. NRF-2015R1A2A1A13001713 grant funded by the Korea government, and 2) Basic Research Laboratory Program through the National Research Foundation of Korea (NRF) No. NRF-2013R1A4A1069575 grant funded by the Ministry of Science, ICT & Future Planning.

CROSS-REFERENCE TO RELATED APPLICATION

This application claims priority to and the benefit of Korean Patent Application No. 10-2014-0177329, filed on Dec. 10, 2014, Korean Patent Application No. 10-2014-0177352, filed on Dec. 10, 2014 and International Patent Application No. PCT/KR2015/013521, filed on Dec. 10, 2015, the disclosure of which is incorporated herein by reference in its entirety.

SEQUENCE LISTING

The Sequence Listing submitted in text format (.txt) filed on Nov. 2, 2017, named "SequenceListing.txt", created on Sep. 12, 2017, (2.72 KB), is incorporated herein by reference.

TECHNICAL FIELD

The present invention relates to an antibacterial composition containing an adenylate kinase or adenosine kinase (ADK) protein derived from *Mycobacterium tuberculosis* as an active ingredient, and a composition for preventing or treating infectious diseases. In addition, the present invention relates to a composition for preventing or treating sepsis or septic shock, which contains the ADK protein and an antibiotic as active ingredients.

BACKGROUND ART

An antibacterial agent is a generic term for antimicrobial agents, and particularly, encompasses substances having antibacterial actions against bacteria, specifically, substances having excellent antibacterial action by inhibiting a bacterial system for synthesizing a cell wall or proteins or products prepared from such substances. Components for an antibacterial agent are mainly extracted from fungi, and have been widely used to treat diseases caused by bacterial infection these days.

Starting with the discovery of the antibacterial agent, penicillin, by Fleming in the 20$^{th}$ century, numerous antibacterial agents and antibiotics have been developed to be free of diseases caused by bacterial infection. These antibacterial agents are an essential part of our life, and have been used in various applications such as food and cosmetic preservatives, as well as medicines. However, in the case of antibacterial agents using chemically synthetic substances, bacteria having resistance to these agents are gradually increasing, and therefore their uses are becoming limited.

Antibacterial agent-resistant bacteria refer to bacteria that have resistance to a specific antibacterial agent and are not affected by a drug action. For example, such bacteria include penicillin-resistant *Staphylococcus aureus* (*S. aureus*), which is not affected by the drug action of penicillin at all. In addition, since first reported in the academic world in 1961, it has been reported that methicillin-resistant *S. aureus* (MRSA) has become a major infectious pathogenic bacterium in the world, vancomycin-resistant *Enterococcus* (VRE) was first found in Europe in 1988, and vancomycin intermediate-resistant *Staphylococcus aureus* (VISA) was found in Japan, the US, France and Korea in the late 1990s. In addition, highly vancomycin-resistant *S. aureus* (VRSA) known as the final agent for treating *S. aureus* infection, which is the most common causative bacteria of human infection, was first reported in the world by the Centers for Disease Control in the US in 2002, and thus possibility of so-called super bacteria spreading is becoming very high.

Meanwhile, sepsis is an inflammatory response caused by excessively activating the immune system in the body due to a cell wall component, that is, lipopolysaccharide (LPS) acting as a toxin, when the human body is infected by pathogenic gram-negative bacteria, and causes an infection in the entire body or is accompanied by shock when symptoms are severe. Specifically, sepsis is generally caused when immunocompromised hosts with humoral immunodeficiency or cellular immunodeficiency such as patients with underlying diseases such as malignant tumors, leukemia, malignant lymphoma, acquired immunodeficiency syndrome (AIDS), collagen disease, renal failure, liver disease, cerebrovascular disorders, diabetes and the like, the aged or premature infants undergo chemotherapy with an adrenal steroid or antitumor agent, radiotherapy such as cobalt irradiation, or treatment such as an indwelling catheter, blood dialysis, organ transplantation, heart surgery, or the like, or a surgery. Sepsis is the main cause of the death of patients hospitalized in an intensive care unit, and a very serious disease generally having a mortality rate of 30% or more. Despite the advances in medical technology, in many cases, sepsis is still caused globally by infection following surgery, and when people with weak immune systems such as infants or the aged are infected, they often develop sepsis in many cases. Representatively, neonatal sepsis is known to occur in approximately 3 out of 1,000 full-term infants, and known to increase by 3 to 4 times in premature infants. When a person develops sepsis, the patient generally undergoes treatment with an antibiotic, but effective treatment may not be achieved only with the antibiotic when bacteria are highly proliferated due to a delay in suitable treatment or infection was made by a strain with strong resistance against antibiotics. Therefore, since pathogenic bacteria having resistance against various antibiotics are gradually increasing, the development of a novel agent for treating sepsis is urgent.

Therefore, the inventors had attempted to develop a novel antibacterial agent and an agent for treating sepsis, thereby confirming that a *Mycobacterium tuberculosis*-derived ADK protein has excellent antibacterial activity selectively against gram-negative bacteria, has excellent effects of inhibiting bacterial proliferation and eliminating endotoxins isolated from dead bacteria, thereby minimizing side effects caused by antibiotics when used in combination with an antibiotic, and has a significantly excellent effect of treating sepsis, compared to single administration, and thus completed the present invention.

DISCLOSURE

Technical Problem

The present invention is directed to providing an antibacterial composition against gram-negative bacteria, which contains an ADK protein as an active ingredient.

The present invention is also directed to providing a composition for preventing or treating infectious diseases, which contains an ADK protein as an active ingredient.

The present invention is also directed to providing a composition for preventing or treating sepsis or septic shock, which contains an ADK protein and an antibiotic as active ingredients.

Technical Solution

To achieve the object, the present invention provides an antibacterial composition, quasi-drug, food additive or feed additive against gram-negative bacteria, which contains an ADK protein as an active ingredient.

The present invention also provides a pharmaceutical composition or food composition for preventing or treating infectious diseases, which contains an ADK protein as an active ingredient.

The present invention also provides a pharmaceutical composition or food composition for preventing or treating sepsis or septic shock, which contains an ADK protein and an antibiotic as active ingredients.

Advantageous Effects

A *Mycobacterium tuberculosis*-derived ADK protein according to the present invention has excellent antibacterial activity selectively against gram-negative bacteria, and can be useful in preventing or treating infectious diseases caused by an antibacterial composition against gram-negative bacteria or gram-negative bacteria. In addition, the ADK protein according to the present invention can have excellent effects of inhibiting bacterial proliferation and eliminating endotoxins isolated from dead bacteria, thereby minimizing side effects caused by antibiotics in combination with an antibiotic, can have a significantly excellent effect of treating sepsis compared to single administration, and can be useful in preventing or treating sepsis or septic shock.

DESCRIPTION OF DRAWINGS

FIG. 6 is a diagram showing that the recombinant ADK protein affects the degree of destruction of a cell surface of *E. coli* and cell organelles, confirmed by TEM analysis.

FIG. 7 is a diagram showing that the ADK protein is specifically migrated only to gram-negative bacteria in animal models.

FIG. 8 is a diagram showing the bacteriocidal effect of the ADK protein on *E. coli* in an animal model.

FIG. 9 is a diagram showing the bacteriocidal effect of the ADK protein on *S. aureus* in an animal model.

MODES OF THE INVENTION

Figure 1:
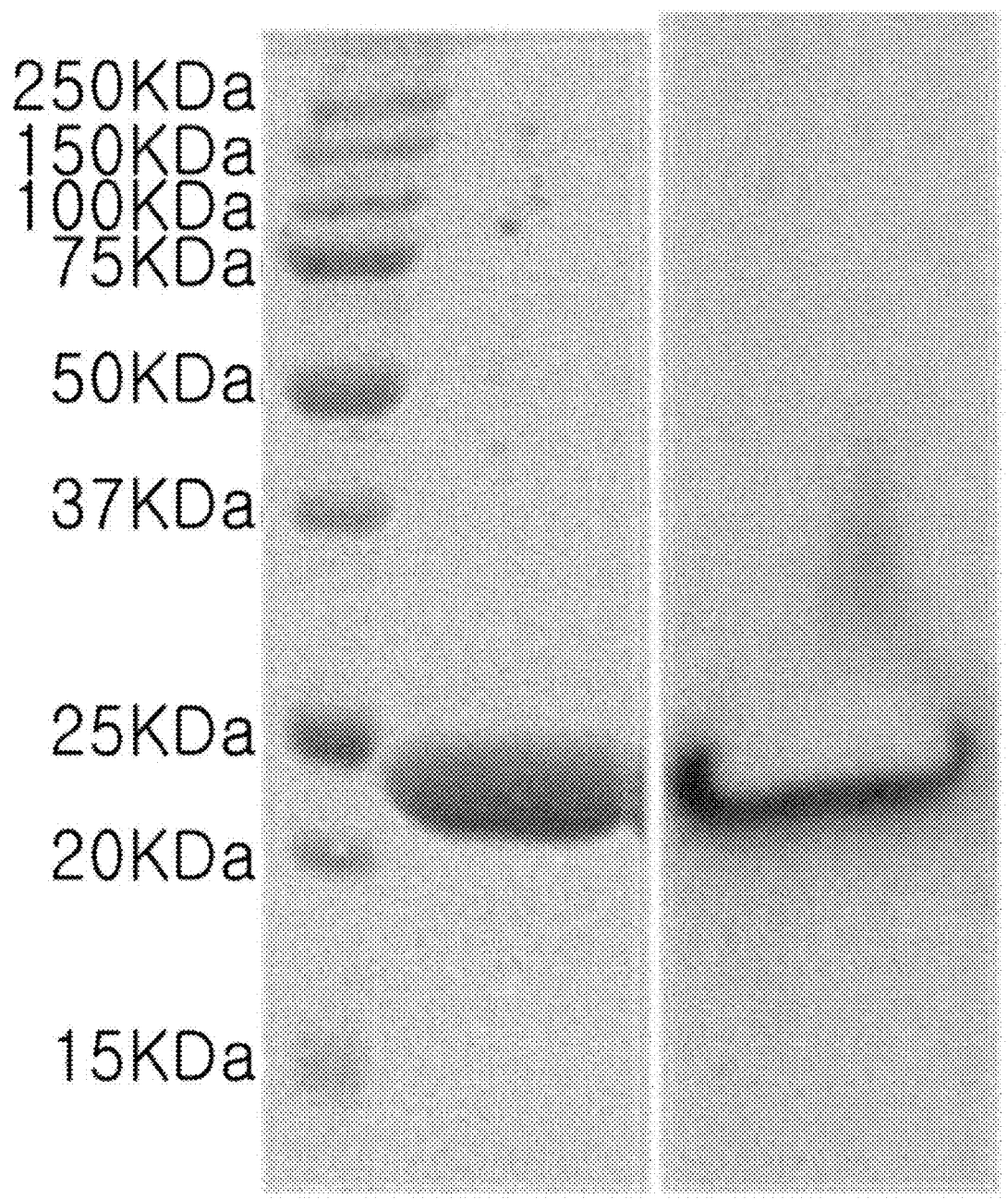
FIG. 1 is a diagram showing a result of confirming a recombinant ADK protein through SDS-PAGE.

Hereinafter, the present invention will be described in further detail.

In one aspect, the present invention provides an antibacterial composition against gram-negative bacteria, which contains an ADK protein as an active ingredient.

The term "antibacterial" or "antibacterial activity" means a resistant property against microorganisms such as bacteria or fungi, and more specifically, a property of an antibiotic substance to inhibit the growth or proliferation of bacteria.

The term "antibacterial composition" is a composition having an activity of inhibiting the growth of microorganisms such as bacteria or fungi, and may include all forms used in various fields requiring an antibacterial effect, for example, medicines, quasi-drugs, food additives, feed additives or the like. Specifically, the antibacterial composition may be used as an antibiotic or anti-contamination agent in the medical field, as a preservative or antibacterial agent in the food field, as an antibacterial, bacteriocidal or sterilizing agent in the agricultural field, in cosmetics or household goods which are products directly related to microorganisms to inhibit dandruff, prevent athlete's foot, prevent armpit odor, and prevent acne, or detergents for cleaning or dish washing as a preservative or an antibacterial or bacteriocidal agent, but the present invention is not limited to the above-mentioned purposes.

The ADK protein of the present invention is derived from *Mycobacterium tuberculosis*, and may consist of an amino acid sequence represented by SEQ ID NO: 1, may be encoded by a base sequence represented by SEQ ID NO: 2, and includes a functional equivalent of the protein. The "functional equivalent" refers to at least 70% or more, preferably 80% or more, more preferably 90% or more, and further more preferably 95% or more sequence homology with the amino acid sequence represented by SEQ ID NO: 1 as a result of addition, substitution or deletion of an amino acid, or a protein having substantially the same quality of physiological activity as the protein consisting of an amino acid sequence represented by SEQ ID NO: 1 or the protein encoded by the base sequence represented by SEQ ID NO: 2.

The ADK protein of the present invention also includes a protein having a wild-type amino acid sequence thereof, and an amino acid sequence variant thereof. A variant of the ADK protein refers to a protein having a different sequence from a native amino acid sequence of the ADK protein by deletion, insertion or non-conservative or conservative substitution of one or more amino acid residues, or a combination thereof. Amino acid exchange in a protein and a peptide, which do not totally change the activity of a molecule, is known in the related art. The ADK protein or a variant thereof may be extracted or synthesized from nature (Merrifield, J. Amer. Chem. Soc. 85:2149-2156, 1963) or prepared by a genetic recombination method based on a DNA sequence (Sambrook et al, Molecular Cloning, Cold Spring Harbor Laboratory Press, New York, USA, 2$^{nd}$ ed., 1989).

The ADK protein of the present invention may be encoded by the base sequence of SEQ ID NO: 2, and a variant capable of having functionally the same action as the nucleotide is included in the scope of the present invention.

The "gram-negative bacteria" refer to bacteria which are red by gram staining, generally have high dye resistance and high surfactant resistance. The gram-negative bacteria of the present invention include all types of gram-negative bacteria containing an endotoxin, for example, strains of *Escherichia, Pseudomonas, Acinetobacter, Salmonella, Klebsiella, Neisseria, Enterobacter, Shigella, Moraxella, Helicobacter, Stenotrophomonas, Bdellovibrio*, and *Legionella* genera, but the present invention is not limited thereto. Specifically, the gram-negative bacteria include *Escherichia coli, Pseudomonas aeruginosa, Pseudomonas fluorescens, Pseudomonas putida, Pseudomonas chlororaphis, Pseudomonas pertucinogena, Pseudomonas stutzeri, Pseudomonas syringae, Acinetobacter baumannii, Acinetobacter lwoffii, Acinetobacter calcoaceticus, Acinetobacter haemolyticus, Salmonella enterica, Salmonella bongori, Salmonella enteritidis, Salmonella typhimurium, Salmonella gallinarum, Salmonella pullorum, Salmonella mbandaka, Salmonella choleraesuis, Salmonella thompson, Salmonella infantis, Salmonella derby, Klebsiella pneumoniae, Klebsiella granulomatis, Klebsiella oxytoca, Klebsiella terrigena, Neisseria gonorrhoeae, Neisseria meningitidis, Enterobacter aerogenes, Enterobacter cloacae, Shigella boydii, Shigella dysenteriae, Shigella flexneri, Shigella sonnei, Moraxella catarrhalis, Moraxella lacunata, Moraxella bovis, Helicobacter pylori, Helicobacter heilmannii, Helicobacter fells, Helicobacter mustelae, Helicobacter fennelliae, Helicobacter rappini, Helicobacter hepaticus, Helicobacter bilis, Helicobacter pullorum, Stenotrophomonas maltophilia, Stenotrophomonas nitritireducens, Bdellovibrio bacteriovorus, Legionella pneumophila, Legionella anisa, Legionella birminghamensis, Legionella bozemanii, Legionella cincinnatiensis, Legionella dumoffii, Legionella feeleii, Legionella gormanii, Legionella hackeliae, Legionella israelensis, Legionella jordanis, Legionella lansingensis, Legionella longbeachae, Legionella maceachernii, Legionella micdadei, Legionella oakridgensis, Legionella sainthelensi, Legionella tucsonensis*, and *Legionella wadsworthii* are included, but the present invention is not limited thereto.

In another aspect, the present invention provides a composition for preventing or treating infectious diseases, which contains an ADK protein as an active ingredient. In still another aspect, the present invention provides a method for preventing or treating infectious diseases, which comprises administering an ADK protein into an individual required for preventing or treating infectious diseases.

The composition includes a pharmaceutical composition or food composition.

The ADK protein of the present invention has excellent antibacterial activity selectively against gram-negative bacteria, and a composition containing the same may be useful in preventing or treating infectious diseases caused by gram-negative bacteria.

The "infectious diseases" used herein are diseases caused by the spread or invasion of pathogens causing illnesses such as viruses, bacteria, fungi or parasites into animals or humans, and refer to all infectious diseases caused by gram-negative bacteria for the purpose of the present invention. For example, the infectious diseases of the present invention include respiratory diseases, gastrointestinal diseases, inflammatory diseases and the like, which are caused by gram-negative bacteria, and specifically, pneumonia, peritonitis, meningitis, wound infections, osteoarthritis, cholecystitis, urinary tract infections, endocarditis, myocarditis, epicarditis, arthritis, pharyngitis, gonorrhea, shigellosis, conjunctivitis, gastritis, tympanitis, cystitis, lymphangitis, sepsis and the like, but the present invention is not limited thereto.

The "prevention" used herein refers to all of the actions for inhibiting or delaying the occurrence of an infectious disease by the administration of the composition, and the "treatment" refers to all of the actions for relieving or beneficially changing the symptoms of an infectious disease by the administration of the composition.

The pharmaceutical composition of the present invention may further include a suitable carrier, excipient or diluent, which is conventionally used. As the carrier, excipient or diluent that can be used in the pharmaceutical composition of the present invention, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate or mineral oil may be used, but the present invention is not limited thereto.

The pharmaceutical composition of the present invention may be administered in an oral or parenteral form according to a conventional method, and is formulated using a filler, a thickening agent, a binder, a wetting agent, a dispersant, a diluent such as a surfactant, or an excipient, which is generally used in formulation. Solid preparations for oral administration include tablets, pills, powder, granules, capsules, etc., and such solid preparations are prepared by mixing at least one excipient, for example, starch, calcium carbonate, sucrose, lactose, gelatin, etc. with the composition. In addition to the simple excipient, lubricants such as magnesium stearate and talc are also used. Liquid preparations for oral administration are suspensions, liquids for internal uses, emulsions, syrups or the like, and may include various excipients, for example, wetting agents, sweeteners, fragrances, preservatives, etc., as well as frequently-used simple diluents, such as water, liquid paraffin, etc. Preparations for parenteral administration include a sterilized aqueous solution, a non-aqueous solvent, a suspension, an emulsion, a lyophilizing agent and a suppository. As the non-aqueous solvent or suspension, propylene glycol or polyethylene glycol, vegetable oil such as olive oil, or an injectable ester such as ethyl oleate may be used. As a base of the suppository, Witepsol, macrogol, Tween 61, cacao butter, laurinum or glycerogelatin may be used.

The "administration" used herein refers to providing of a predetermined pharmaceutical composition of the present invention to an individual by a suitable method.

A preferable dosage of the pharmaceutical composition of the present invention may be suitably selected by those of ordinary skill in the art according to the condition and body weight of an individual, severity of a disease, a drug form, an administration route and duration. For preferable effects, the pharmaceutical composition of the present invention may be administered daily at 0.001 to 1000 mg/kg. The administration may be performed once or several times a day. The dosage does not limit the scope of the present invention in any aspect.

The pharmaceutical composition of the present invention may be administered into an individual via various routes. All methods of administration may be expected, and the pharmaceutical composition of the present invention may be administered, for example, orally, or by rectal, intravenous, intramuscular, subcutaneous, interuterine dura mater or intracerebroventricular injection. However, in oral administration, since a protein is digested, an oral composition may be prepared in a form in which an active agent is coated or is protected from the decomposition in the stomach. The composition of the present invention may be administered in an injection.

The pharmaceutical composition of the present invention may further include one or more of the known substances having antibacterial activity, as well as the ADK protein.

In the present invention, the food composition may be prepared in the form of health functional foods.

In the present invention, the health functional foods refer to a group of foods imparting an added value to exert and express the function of corresponding food according to a specific purpose using physical, biochemical, bioengineering techniques to foods, or processed foods designed to sufficiently express body modulating functions relating to regulation of biological defense rhythm with the food composition, disease prevention and recovery, etc. with respect to the living body.

The health functional food may include a supplementary food additive, which is sitologically acceptable, and may further include a suitable carrier, excipient and diluent, which are conventionally used in the preparation of the health functional food.

When the food composition of the present invention is used as a food additive, the composition may be added as it is, used together with other food or a food component, and suitably used according to a conventional method. A mixed amount of the active ingredient may be suitably determined according to a purpose of use (preventive, health or therapeutic treatment). Generally, in food or beverage preparation, the composition of the present invention is added at 15 wt % or less, and preferably 10 wt % or less with respect to raw substances. However, in the case of long-term ingestion, for the purposes of health and hygiene or health control, the amount of composition added may be in the above range or less, and since there is no problem in terms of safety, the active ingredient may be used in an amount also in the range or more.

Other than the above ingredients, the food composition of the present invention may include various nutrients, vitamins, electrolytes, flavoring agents, coloring agents, pectic acid and a salt thereof, alginic acid and a salt thereof, organic acids, protective colloidal thickening agents, pH adjusters, stabilizers, preservatives, glycerin, alcohols, or a carbonated agent used in carbonated beverages. In addition, the food composition of the present invention may include natural fruit juice, fruit juice beverages, or fruit flesh for manufacturing vegetable beverages. Such components may be used independently or in combination. A ratio of such additives does not matter much, but is generally selected from a range of 0.01 to 0.1 parts by weight per 100 parts by weight of the composition of the present invention.

In yet another aspect, the present invention provides a composition for preventing or treating sepsis or septic shock, which comprises the ADK protein and an antibiotic as an active ingredient. In yet another aspect, the present invention provides a method for preventing or treating sepsis or septic shock, which comprises administering the ADK protein and an antibiotic to an individual required for preventing or treating sepsis or septic shock.

The composition includes a pharmaceutical composition and a food composition.

The "sepsis" used herein refers to a condition exhibiting a serious inflammatory response in the whole body due to the infection with microorganisms. When there are two or more symptoms of hyperpyrexia in which a body temperature is increased to 38° C. or more, hypothermia in which a body temperature is decreased to 36° C. or less, an increase in the breathing rate to 24 breaths or more per minute (tachypnea), a heart rate of 90 times per minute (tachycardia), and a noticeable increase or decrease in the number of white blood cells in a blood test, it is called systemic inflammatory response syndrome (SIRS). When the SIRS is caused by infection with microorganisms, it is called sepsis. Pathogenic bacteria continuously or intermittently enter the blood stream to lesions of infection in a body and settle in various organ tissues to form lesions and show severe systemic symptoms. Causative organisms are *Staphylococcus, Streptococcus, Escherichia coli, Pseudomonas aeruginosa, Mycobacterium tuberculosis, Pneumococcus*, fungi, anaerobic bacteria, etc.

The "antibiotics" refer to substances used to treat and prevent bacterial infection, and substances that inhibit the growth or life of microorganisms. The antibiotics include all of natural antibiotics, which are chemicals produced by microorganisms such as bacteria or fungi, semi-synthetic antibiotics, which are derivatives obtained by changes in structural form of antibiotics, and synthetic antibiotics (antibacterial agent) which are chemically synthesized.

The antibiotics of the present invention include, but are not limited to, aminoglycoside-, penicillin-, cephalosporin-, tetracycline-, macrolide-, streptogramin-, glycopeptide-, peptide-, flavophospholipol-, polyether-, phenicol-, lincosamide-, rifamycin-, polyene-, sulfonamide-, benzylpyrimidine-, quinolone-, fluoroquinolone-, and nitrofuran-based antibiotics.

The aminoglycoside-based antibiotics include, but are not limited to, gentamicin, kanamycin, ribostamycin, tobramycin, sisomicin, astromicin, isepamicin, arbekacin, dibekacin, spectinomycin, netilmicin, micronomycin, streptomycin, dihydrostreptomycin, apramycin, destomycin, hygromycin, amikacin, neomycin, etc.

The penicillin-based antibiotics include, but are not limited to, penicillin, benzylpenicillin, oxacillin, cloxacillin, dicloxacillin, flucloxacillin, nafcillin, ampicillin, amoxicillin, carbenicillin, ticarcillin, piperacillin, etc.

The cephalosporin-based (cephem-based) antibiotics include, but are not limited to, cephalothin, cephazolin, cephaloridine, cephalexin, cephacetrile, cephalonium, cefoxazole, cefapirin, cefadroxil, cefamandole, cefoxitin, cefuroxime, cefoperazone, cefmetazole, cefotaxime, ceftiofur, etc.

The tetracycline-based antibiotics include, but are not limited to, chlortetracycline, oxytetracycline, tetracycline, minocycline, doxycycline, etc.

The macrolide-based antibiotics include, but are not limited to, erythromycin, kitasamycin, spiramycin, oleandomycin, josamycin, sedecamycin, tylosin, roxithromycin, etc.

The streptogramin-based antibiotics include, but are not limited to, virginiamycin, mikamycin, etc.

The glycopeptide-based antibiotics include, but are not limited to, avoparcin, vancomycin, etc.

The peptide-based antibiotics include, but are not limited to, polymyxins (e.g., colistin and polymyxin B), cyclic peptides (e.g., bacitracin), cyclic depsipeptides (e.g., enramycin and thiopeptin), etc.

The flavophospholipol-based antibiotics include, but are not limited to, bambermycin, macabomycin, quebemycin, etc.

The polyether-based antibiotics include, but are not limited to, monensin, salinomycin, lasalocid, narasin, maduramycin, etc.

The phenicol-based antibiotics include, but are not limited to, chloramphenicol, thiamphenicol, florfenicol, etc.

The lincosamide-based antibiotics include, but are not limited to, lincomycin, clindamycin, etc.

The rifamycin-based antibiotics include, but are not limited to, rifampicin, etc.

The polyene-based antibiotics include, but are not limited to, nystatin, pimaricin, pentamycin, amphotericin B, trichomycin, candicidin, etc.

The sulfonamide-based antibiotics include, but are not limited to, sulfapyridine, sulfadiazine, sulfadimidine, sulfafurazole, sulfamonomethoxazole, etc.

The benzylpyrimidine-based antibiotics include, but are not limited to, trimethoprim, ormetoprim, tetroxoprim, etc.

The quinolone-based antibiotics include, but are not limited to, nalidixic acid, oxolinic acid, cinoxacin, acrosoxacin, etc.

The fluoroquinolone-based antibiotics include, but are not limited to, flumequine, ciprofloxacin, enoxacin, fleroxacin, marbofloxacin, etc.

The nitrofuran-based antibiotics include, but are not limited to, furazolidone, furaltadone, nitrovin, nitrofurazone, etc.

A mixing ratio of the ADK protein and the antibiotic in the composition is not limited, and may be suitably controlled within concentration ranges in which side effects are exhibited and therapeutic effects are exhibited according to the type of an antibiotic.

An ADK protein derived from *Mycobacterium tuberculosis* according to the present invention has excellent effects of eliminating endotoxins isolated from dead bacteria, as well as inhibiting bacterial proliferation, and therefore may minimize side effects caused by an antibiotic in combination with the antibiotic, and have a significantly excellent sepsis treating effect, compared to single administration.

Therefore, the ADK protein and antibiotic of the present invention may be useful for a medicine for preventing or treating sepsis or septic shock and health functional food.

Since the composition for preventing or treating sepsis or septic shock includes a pharmaceutical composition and a food composition, duplicate contents of the above-described pharmaceutical composition and food composition will not be described to avoid excessive complexity of the specification caused by the duplicated contents.

Hereinafter, exemplary examples will be provided to help in understanding of the present invention. However, the following examples are merely provided to facilitate understanding of the present invention, and the scope of the present invention is not limited to the following examples.

Example 1. Cloning of Recombinant ADK

An ADK (Rv0733) site was amplified by PCR using genomic DNA (ATCC 27294) of *Mycobacterium tuberculosis* H37Rv as a template (primers: 5'-CATATGAGAGTTTTGTTGCTGGGACCG-3' and 5'-AAGCTTCTTTCCCAGAGCCCGCAACGC-3'). An isolated PCR product was cleaved with NdeI and HindIII restriction enzymes, and inserted into an expression vector, pET22b vector. *E. coli* BL21 transformed by the ADK gene-inserted pET22b vector was transferred to an LB broth (containing 100 μg/ml ampicillin), and cultured for 12 hours at 37° C. Afterward, 1 mM of isopropyl-D-thiogalactopyranoside (IPTG) was added to the resulting cells which were then cultured again for 6 hours and dissolved in a lysis buffer (containing 1M DTT, lysozyme and PMSF). A recombinant protein was purified using nickel-nitrilotriacetic acid (Ni-NTA, Invitrogen, Carlsbad, Calif., USA) agarose according to the manufacturer's method. Finally, the purified recombinant ADK protein was analyzed and confirmed by SDS-PAGE, reconfirmed by sequencing (SEQ ID NO: 1), and then quantified using a Bradford assay. The result of confirming the recombinant ADK protein through SDS-PAGE is shown in FIG. 1.

Experimental Example 1. Verification of Antibacterial Activity of ADK Protein

To verify the antibacterial activity of the recombinant ADK protein obtained in Example 1, the effect of the ADK protein on the growth of gram-negative bacteria such as *E. coli* and *P. aeruginosa* and a gram-positive bacterium such as *S. aureus* was analyzed.

More specifically, $1 \times 10^5$ CFU of strains were put into a 10 ml LB broth, and an antibiotic (ampicillin) and the ADK protein were added respectively according to five conditions as follows (Group 1: LB broth media with 100 μg/ml ampicillin, Group 2: LB broth media with 20 μg/ml Adk, Group 3: LB broth media with 50 μg/ml Adk, Group 4: LB broth media with 100 μg/ml Adk, Group 5: Non-antibacterial agent LB broth media). The strains were cultured in a 37° C. shaking incubator, 100 μl aliquots of each group was taken at 3-hour intervals and diluted with an LB broth in predetermined ratios, followed by plating the resulting cells on an LB agar (Biobasic, Amherst, N.Y.) plate. The cells were cultured again in a 37° C. incubator overnight, and then CFU values over time were calculated by counting the number of colonies on the LB agar plate. The results are shown in FIGS. 2 to 4.

Figure 2:
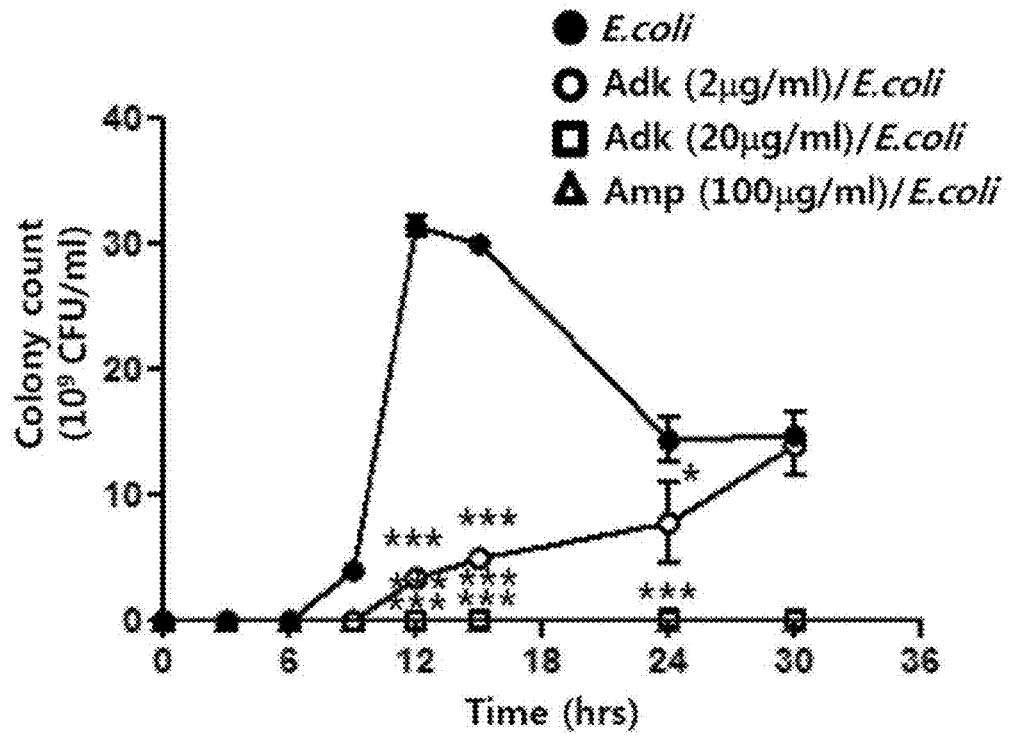
FIG. 2 is a diagram showing that the recombinant ADK protein affects the growth of *Escherichia coli* (*E. coli*).
Figure 3:
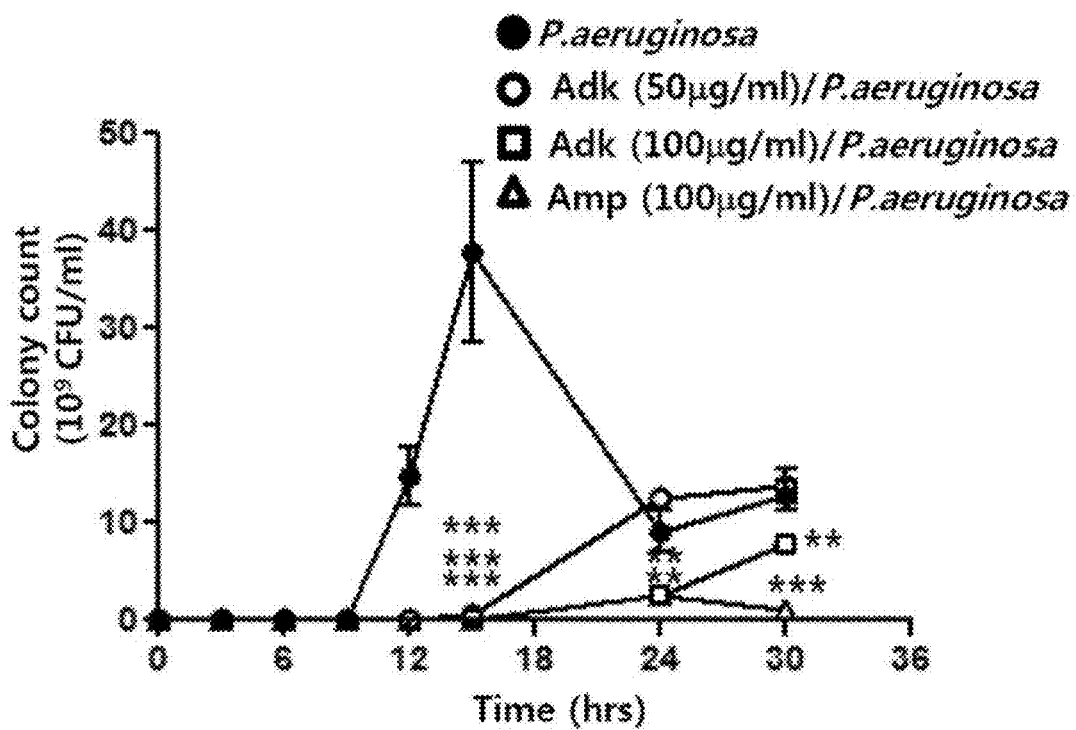
FIG. 3 is a diagram showing that the recombinant ADK protein affects the growth of *Pseudomonas aeruginosa* (*P. aeruginosa*).
Figure 4:
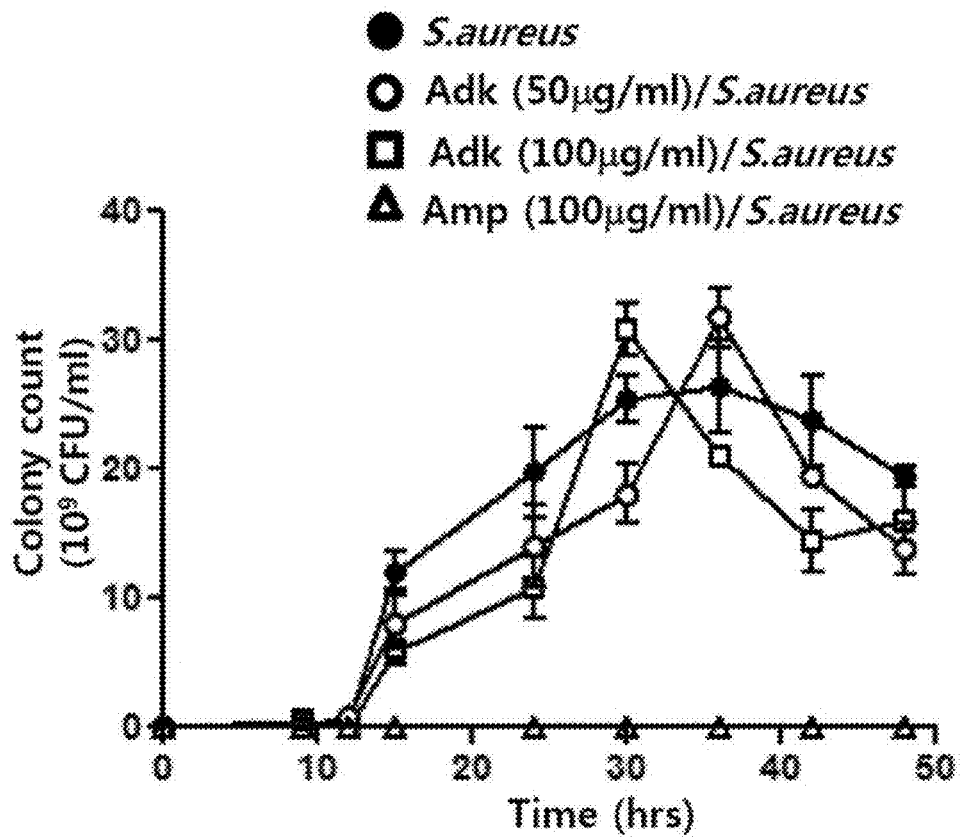
FIG. 4 is a diagram showing that the recombinant ADK protein affects the growth of *S. aureus*.

As shown in FIGS. 2 to 4, it was confirmed that the ADK protein inhibited the growth of the gram-negative bacteria, E. coli and P. aeruginosa, but did not specifically affect the growth of the gram-positive bacterium, S. aureus. However, the known antibiotic, ampicillin, inhibited all of the gram-negative bacteria and the gram-positive bacterium. Accordingly, it was confirmed that the ADK protein of the present invention had an antibacterial effect specifically on the gram-negative bacteria.

Experimental Example 2. MIC and MBC Analyses

To confirm a suitable concentration at which the recombinant ADK protein has an inhibitory effect on the growth of various types of gram-negative bacteria and gram-positive bacteria, a minimum inhibitory concentration (MIC) and a minimum bactericidal concentration (MBC) were measured.

More specifically, one colony of each strain (*Escherichia coli* DH5α, *Escherichia coli* K1, *Acinetobacter baumannii* (ATCC 19606), *Pseudomonas aeruginosa*, *Salmonella enteritidis* (ATCC 13076), *Salmonella typhimurium*, *Klebsiella pneumoniae* (ATCC 13883), *Staphylococcus aureus* USA:300, *Staphylococcus epidermidis*, *Bacillus subtilis*) was isolated, cultured in a 10 ml Mueller-Hinton (MH) broth (OXOID, Hampshire, UK) for 6 hours, and then each strain was diluted with a MEI broth to obtain the O.D. at 625 nm of 0.1 (McFarland 0.5) using a spectrophotometer. The diluted strain was diluted 1/20 fold in saline (0.09% NaCl). Various concentrations of antibiotics (ampicillin, gentamicin, levofloxacin, imipenem) and the ADK protein were respectively added to a 96-well culture plate to which 100 µl of a MH broth was added, and 9 µl of the diluted strain was added to each well and cultured overnight.

An MIC was calculated using a resazurin microtiter assay (REMA), 30 µl of a 0.01% resazurin (ACROS Organics, N.J.) solution was added to each well of the 96-well culture plate, and then cultured at 37° C. for 1 hour. When the medium in each well was dark blue, it indicated that the strains were not grown, and when pink, it indicated that the strains were well grown. Such color changes was detected by measuring the O.D. at 505 nm using a spectrophotometer, and the resulting value of a well that was not treated with neither an antibiotic nor the ADK protein was predetermined as 100% to calculate 50% and 80% inhibition concentrations.

Also, to measure an MBC, 10 µl aliquots were taken from each well of the 96-well culture plate, plated on an LB agar plate, and cultured at 37° C. overnight, followed by calculating a concentration at which no colony was grown.

The above-described experimental results are shown in Table 1.

TABLE 1

| Organisms and antimicrobial agent | MIC (µg/ml) | | | MBC (µg/ml) |
|---|---|---|---|---|
| | Testing range | 50% | 80% | |
| *Escherichia coli* DH5a | | | | |
| Ampicillin | 0.45~500 | <2.0 | <4.0 | <7.8 |
| Gentamicin | 0.45~500 | <0.5 | <1.0 | <1.0 |
| Levofloxacin | 0.45~500 | <0.5 | <1.0 | <1.0 |
| Imipenem | 0.45~500 | <3.9 | <7.8 | <7.8 |
| Adk | 0.45~500 | <3.9 | <7.8 | <7.8 |
| *Escherichia coli* K1 | | | | |
| Ampicillin | 0.45~500 | <3.9 | <7.8 | <7.8 |
| Gentamicin | 0.45~500 | <0.5 | <1.0 | <1.0 |
| Levofloxacin | 0.45~500 | <0.5 | <1.0 | <1.0 |
| Imipenem | 0.45~500 | <0.5 | <1.0 | <1.0 |
| Adk | 0.45~500 | <1.0 | <2.0 | <3.9 |
| *Acinetobacter baumannii* | | | | |
| Ampicillin | 0.45~500 | <31.3 | <62.5 | <62.5 |
| Gentamicin | 0.45~500 | <1.0 | <2.0 | <2.0 |
| Levofloxacin | 0.45~500 | <0.5 | <1.0 | <2.0 |
| Imipenem | 0.45~500 | <7.8 | <15.6 | <15.6 |
| Adk | 0.45~500 | <2.0 | <3.9 | <3.9 |

TABLE 1-continued

| | | | | | |
|---|---|---|---|---|---|
| *Pseudomonas aeruginosa* | | | | | |
| Ampicillin | 0.45~500 | <125 | <250 | <500 | Gram-negative bacteria |
| Gentamicin | 0.45~500 | <0.5 | <1.0 | <1.0 | |
| Levofloxacin | 0.45~500 | <0.5 | <1.0 | <2.0 | |
| Imipenem | 0.45~500 | <31.3 | <62.5 | <125 | |
| Adk | 0.45~500 | <2.0 | <3.9 | <3.9 | |
| *Salmonella enteritidis* | | | | | |
| Ampicillin | 0.45~500 | <3.9 | <7.8 | <7.8 | |
| Gentamicin | 0.45~500 | <0.5 | <1.0 | <1.0 | |
| Levofloxacin | 0.45~500 | <0.5 | <1.0 | <1.0 | |
| Imipenem | 0.45~500 | <3.9 | <7.8 | <15.6 | |
| Adk | 0.45~500 | <7.8 | <15.6 | <15.6 | |
| *Salmonella typhimurium* | | | | | |
| Ampicillin | 0.45~500 | <1.0 | <2.0 | <2.0 | |
| Gentamicin | 0.45~500 | <0.5 | <1.0 | <1.0 | |
| Levofloxacin | 0.45~500 | <0.5 | <1.0 | <1.0 | |
| Imipenem | 0.45~500 | <3.9 | <7.8 | <7.8 | |
| Adk | 0.45~500 | <31.3 | <62.5 | <125 | |
| *Klebsiella pneumoniae* | | | | | |
| Ampicillin | 0.45~500 | <125 | <250 | <250 | |
| Gentamicin | 0.45~500 | <0.5 | <1.0 | <1.0 | |
| Levofloxacin | 0.45~500 | <0.5 | <1.0 | <1.0 | |
| Imipenem | 0.45~500 | <2.0 | <7.8 | <31.3 | |
| Adk | 0.45~500 | <62.5 | <125 | <250 | |
| *Staphylococcus aureus* | | | | | |
| Ampicillin | 0.45~500 | <1.0 | <2.0 | <15.6 | |
| Gentamicin | 0.45~500 | <0.5 | <1.0 | <2.0 | |
| Levofloxacin | 0.45~500 | <0.5 | <1.0 | <1.0 | |
| Imipenem | 0.45~500 | <0.5 | <1.0 | <1.0 | |
| Adk | 0.45~500 | no effect | no effect | no effect | |
| *Staphylococcus epidermidis* | | | | | |
| Ampicillin | 0.45~500 | <250 | <500 | <500 | Gram-positive bacteria |
| Gentamicin | 0.45~500 | <0.5 | <1.0 | <1.0 | |
| Levofloxacin | 0.45~500 | <0.5 | <0.5 | <0.5 | |
| Imipenem | 0.45~500 | <0.5 | <0.5 | <0.5 | |
| Adk | 0.45~500 | no effect | no effect | no effect | |
| *Bacillus subtillis* | | | | | |
| Ampicillin | 0.45~500 | <0.5 | <1.0 | <2.0 | |
| Gentamicin | 0.45~500 | <0.5 | <1.0 | <1.0 | |
| Levofloxacin | 0.45~500 | <0.5 | <0.5 | <0.5 | |
| Imipenem | 0.45~500 | <0.5 | <0.5 | <0.5 | |
| Adk | 0.45~500 | no effect | no effect | no effect | |

As shown in Table 1, it was confirmed that the ADK protein inhibited the growth of all types of gram-negative bacteria used in the experiment, and exhibited bacteriocidal effects against the bacteria, but did not specifically affect the growth and survival of the gram-positive bacteria, *Staphylococcus aureus, Staphylococcus epidermidis*, and *Bascillus subtilis*, and exhibited an antibacterial effect specifically on the gram-negative bacteria.

Experimental Example 3. SEM Analysis

To confirm the effect of the recombinant ADK protein on the morphology of cells, following treatment of the recombinant ADK protein to *E. coli* over time, a scanning electron microscope (SEM) analysis was performed.

More specifically, following the addition of 100 ng/ml ampicillin (used as a positive control) or 20 ng/ml ADK protein to 10 ml of an LB broth, *E. coli* K1 was shake-cultured at 37° C. for a period of time. The cultured *E. coli* was washed with 1×PBS three times, and fixed with 1 ml of a 2.5% glutaraldehyde (Sigma-Aldrich, St. Louis, Mo.) solution. The sample was observed using LEO 1455 VP SEM (Carl Zeiss, Oberkochen, Germany). A negative control (Control) received no treatment. A result is shown in FIG. 5.

Figure 5:
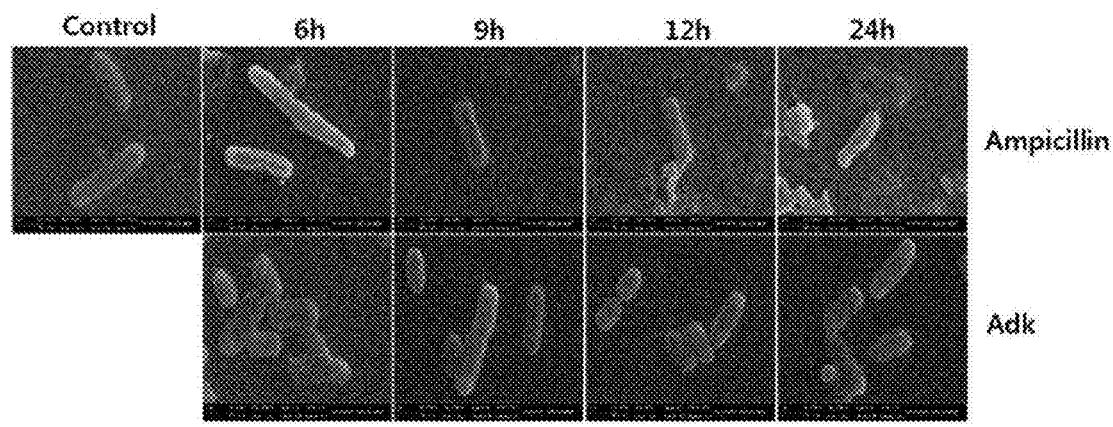
FIG. 5 is a diagram showing that the recombinant ADK protein affects morphology of *E. coli* cells, confirmed by SEM analysis.

As shown in FIG. 5, it was confirmed that *E. coli* in the negative control (Control) has a bright and smooth cell surface, and in the ADK protein-treated group, a surface of *E. coli* is peeled off, and apoptosis occurs.

Experimental Example 4. TEM Analysis

To confirm the effect of the recombinant ADK protein on the degree of destruction of a cell surface and cell organelles, E. coli was treated with the recombinant ADK protein, and after 12 hours, transmission electron microscopy (TME) using gold nanoparticles was performed according to a known method. A negative control (Control) received no treatment. A result is shown in FIG. 6.

As shown in FIG. 6, it was observed that, in the case of E. coli in the negative control (Control), a cell surface was uniformly maintained, nanoparticles entered into the cell, and no destruction was shown, and in the case of a group treated with ADK protein-coated gold nanoparticles, the cell wall of E. coli was lost and apoptosis simultaneously occurred inside the cell (appearing white).

Experimental Example 5. Verification of Gram-Negative Selective Antibacterial Activity of ADK Protein Using Animal Model To confirm whether the recombinant ADK protein selectively binds to gram-negative bacteria in an animal model, an experiment was performed as follows.

First, gram-negative bacteria, E. coli K1 or Pseudomonas aeruginosa, were subcutaneously injected into the left sides of the backs of CAnN.Cg-Foxn1 nu/CrljOri mice at a concentration of $10^7$ CFU/mouse, and a gram-positive bacterium, S. aureus, was subcutaneously injected into the right sides of the backs of the mice at the same concentration. 200 μg/mouse of IRDye800-conjugated ADK was intravenously injected into the tails of the mice. Three hours after the injection, the translocation and position of the ADK protein were observed using a near-infrared (NIR) fluorescence imaging system. A result is known in FIG. 7.

As shown in FIG. 7, it was confirmed that the ADK protein specifically migrates to the gram-negative bacteria (E. coli K1 or P. aeruginosa).

In addition, to confirm that the recombinant ADK protein selectively binding to the gram-negative bacteria in animal models has a bacteriocidal effect against the gram-negative bacteria, gram-negative bacteria, E. coli K1, or gram-positive bacteria, S. aureus ($10^7$ CFU/mouse), which was stained with IRDye800, and FITC-conjugated ADK (200 μg/mouse) were intraperitoneally injected into CAnN.Cg-Foxn1 nu/CrljOri mice, and bacteriocidal effects over time were observed using a near-infrared (NIR) fluorescence imaging system. In addition, 24 hours after the injection, each organ was removed to confirm the presence of corresponding strains. Results are shown in FIGS. 8 to 10.

As shown in FIG. 8, it was confirmed that, in a group into which only IRdye800-conjugated E. coli was injected, until 24 hours after the injection, a certain amount of E. coli existed in the peritoneal cavity in the mice, but a group treated with FITC-conjugated ADK in combination had a significantly decreased survival rate of E. coli in the peritoneal cavity of the mice, followed by complete elimination of E. coli 24 hours after the injection. In addition, the ADK protein was also released outside after 24 hours.

However, as shown in FIG. 9, it was confirmed that in a group in which IRdye800-conjugated S. aureus was injected, the treatment in combination with FITC-conjugated ADK did not affect the survival rate of S. aureus existing in the peritoneal cavity of the mice.

Figure 10:
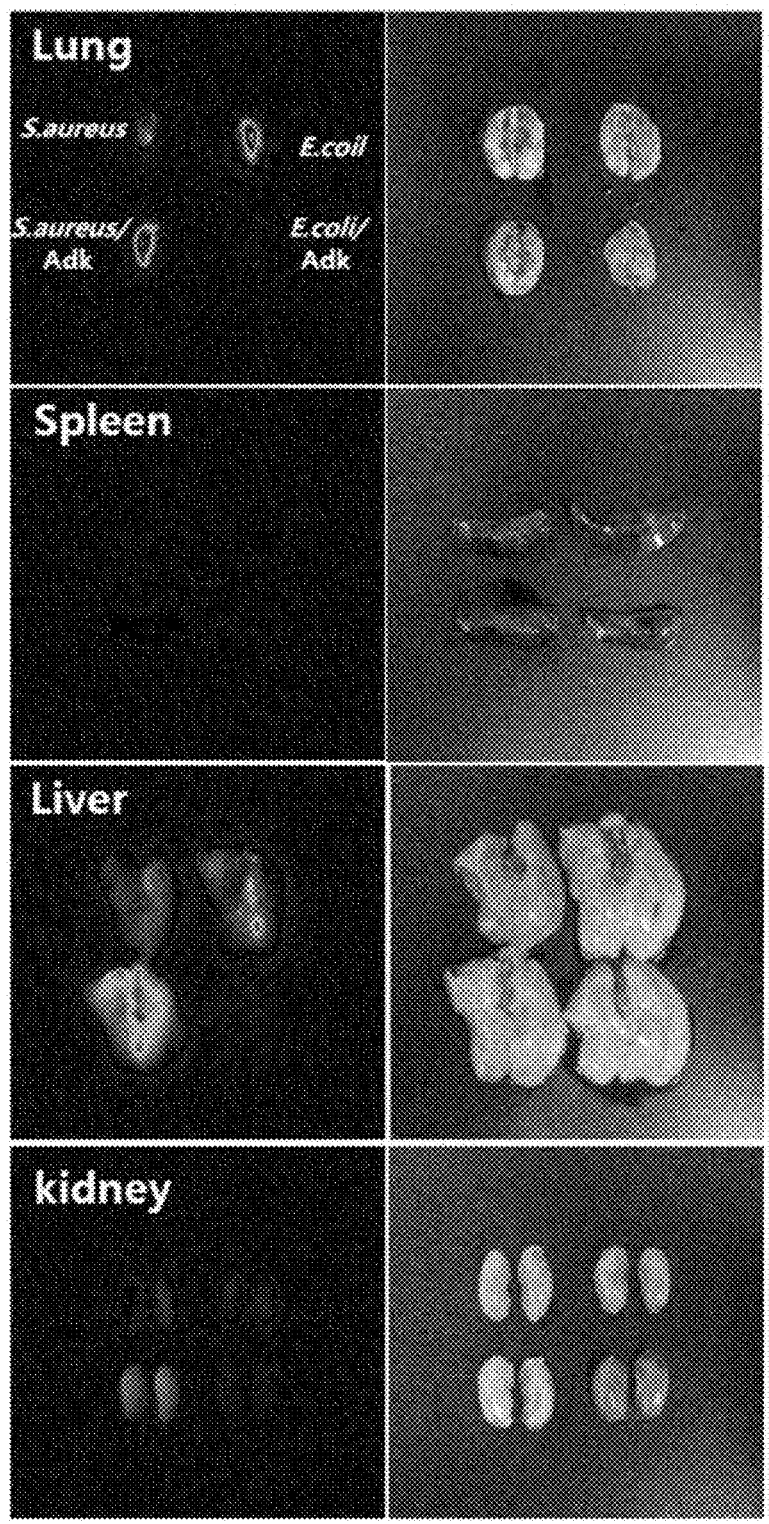
FIG. 10 is a diagram showing the bacteriocidal effect of the ADK protein on each tissue in an animal model.

In addition, as shown in FIG. 10, it was confirmed that a gram-negative bacterium, E. coli, was completely eliminated by the ADK protein from all of the lung, spleen, liver and kidney tissues of the mice.

From the above-described experimental results, it was confirmed that the Mycobacterium tuberculosis-derived ADK protein has excellent antibacterial activity selectively against the gram-negative bacteria.

Experimental Example 6. Analysis of Therapeutic Effect of Combined Administration of ADK Protein and Antibiotic in Sepsis Animal Model To analyze the therapeutic effect of the combined administration of the ADK protein and an antibiotic in a sepsis animal model, an experiment was performed as follows.

6-1. Experimental Design and Analysis of Survival Rate

Figure 11:
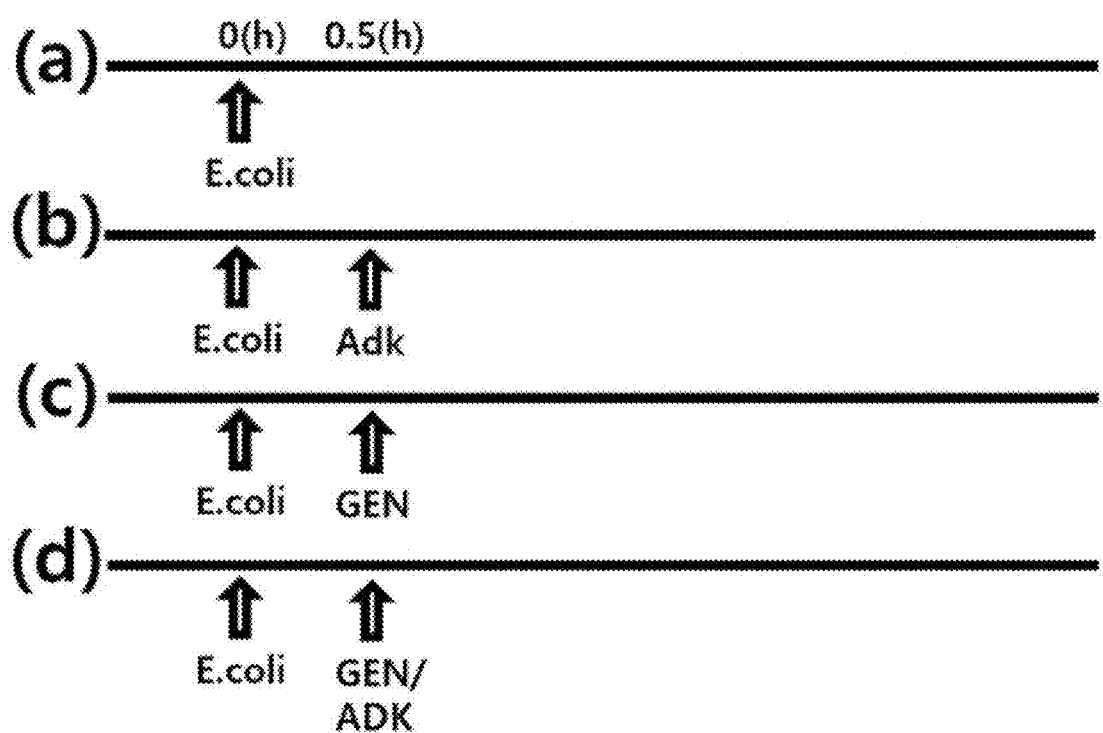
FIG. 11 is a diagram showing an animal test design for confirming a sepsis treatment effect.

Six-week-old female BALB/c mice were used as laboratory animals. E. coli K1 (in LB broth) was injected into the peritoneal cavity of the mice at a dose of $10^7$ CFU/mouse to induce sepsis. After the injection of E. coli K1, a type of aminoglycoside-based antibiotic, gentamicin (GEN, 100 μg/kg) and/or Adk (100 μg/mouse) were/was intraperitoneally injected. A negative control (CON, Control) received no treatment. The above-described experimental design and experimental groups are shown in FIG. 11, and a survival rate of each mouse over time is shown in FIG. 12.

Figure 12:
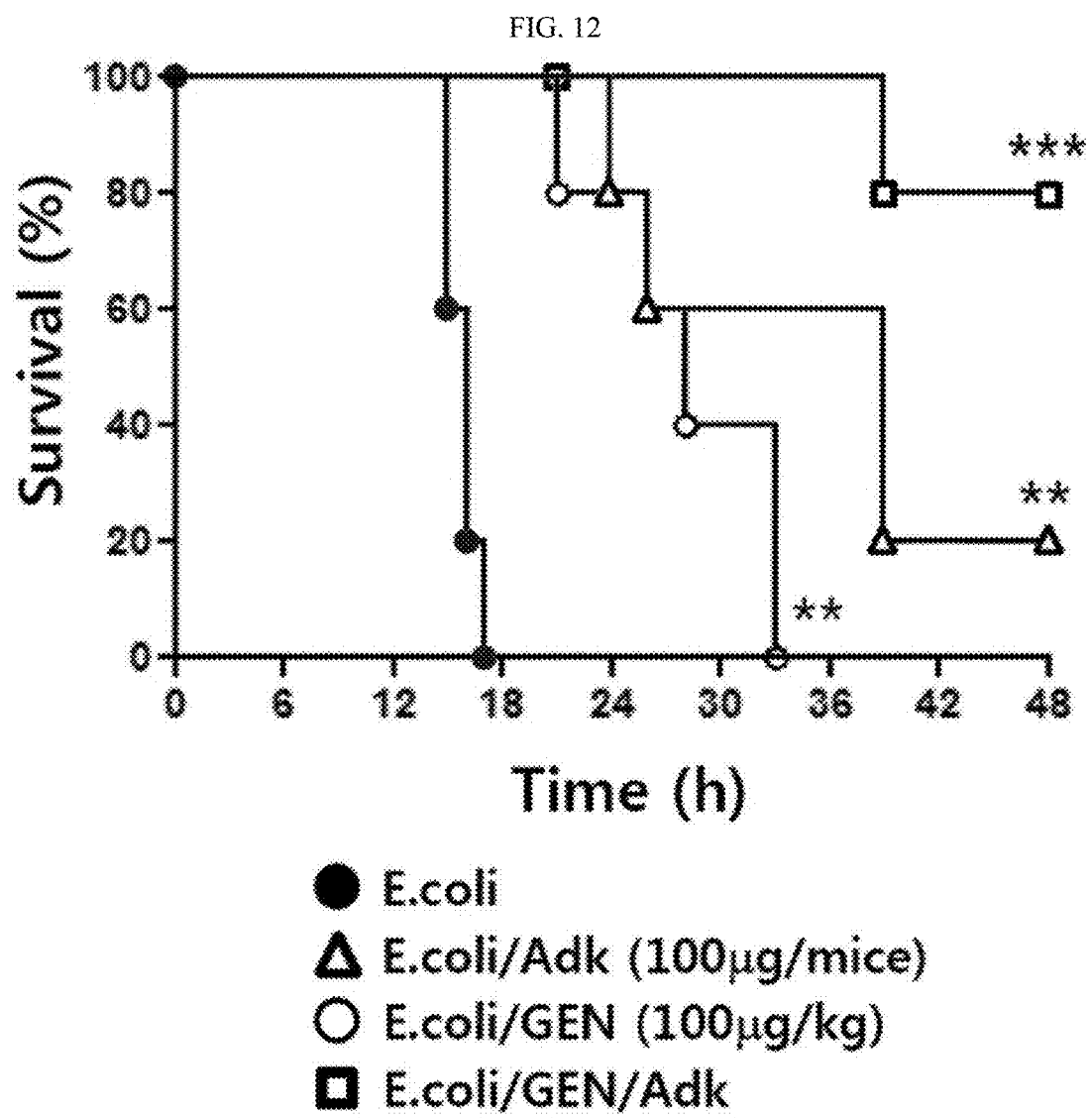
FIG. 12 is a diagram showing viability according to time when the ADK protein or an antibiotic (gentamicin) is administered to a sepsis animal model.

As shown in FIG. 12, in the negative control treated with nothing, all mice were dead 18 hours after sepsis induction, and in a gentamicin-only group, all mice were also dead 30 hours after sepsis induction. However, it was confirmed that, in a group in which the ADK protein was administered in combination with gentamicin, a survival rate was 80% 48 hours after sepsis induction, which was significantly increased, compared to the negative control (blue line).

6-2. Serum Analysis

Twelve hours after sepsis induction, levels of inflammatory cytokines (TNF-α, IL-6, and IL-1β), AST, ALT, BUN, and endotoxins in sera isolated from mice were analyzed. Here, a cytokine concentration was measured using an ELISA kit (eBiosciences, San Diego, Calif.), and endotoxins were analyzed using an endotoxin detection kit (LAL assay kit, Thermo Fisher Scientific, Bremen, Germany). Results are shown in FIGS. 13 to 15.

Figure 13:
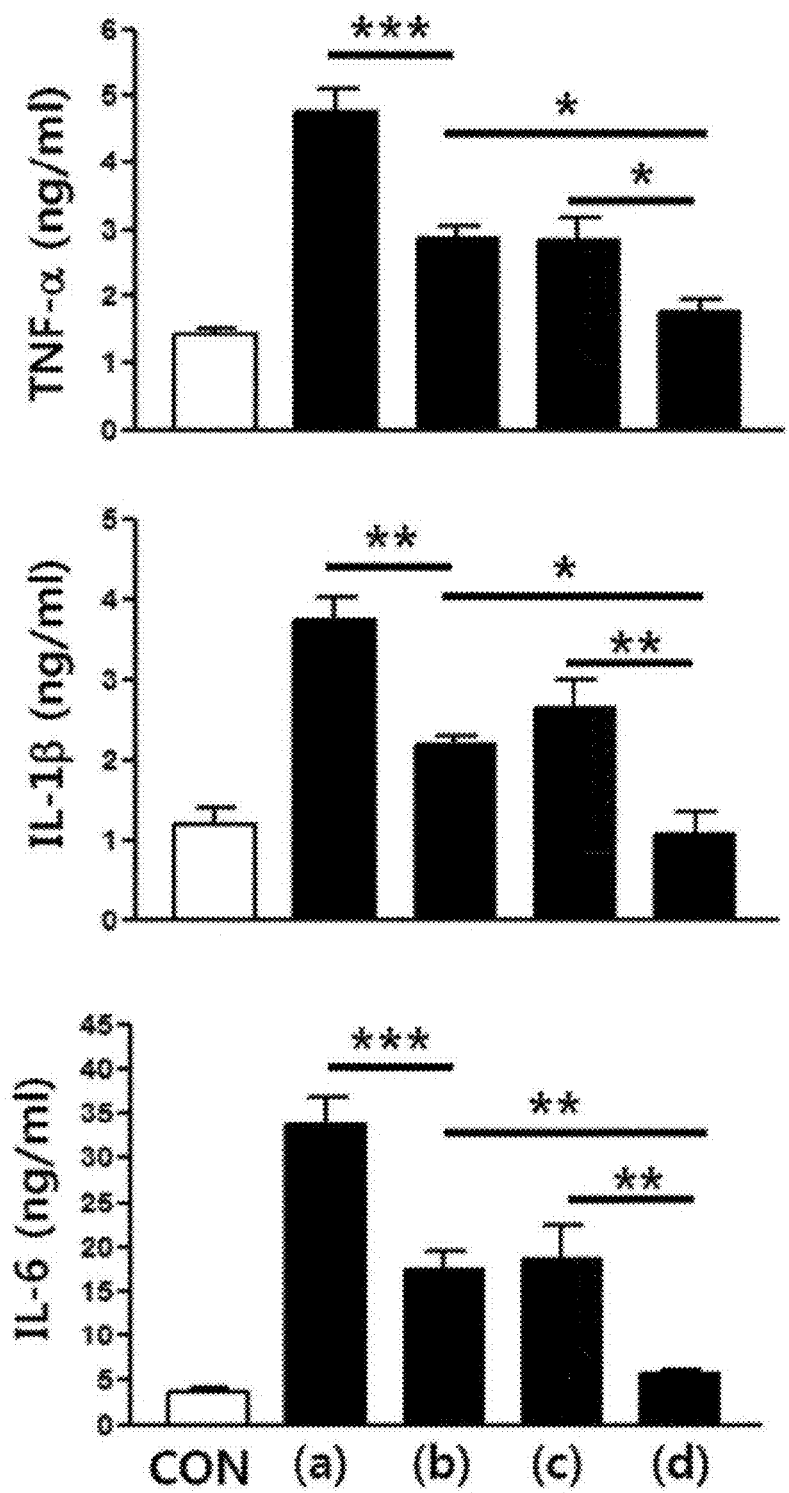
FIG. 13 is a diagram showing the amounts of inflammatory cytokines (TNF-α, IL-1β, IL-6) in serum when the ADK protein or an antibiotic (gentamicin) is administered to a sepsis animal model.

As shown in FIG. 13, it was confirmed that, in the negative control (CON), when the ADK protein was administered in combination with gentamicin, amounts of inflammatory cytokines such as TNF-α, IL-6 and IL-1β in mouse sera, which were increased by sepsis, were significantly decreased, and had a significant difference from the single treatment group.

Figure 14:
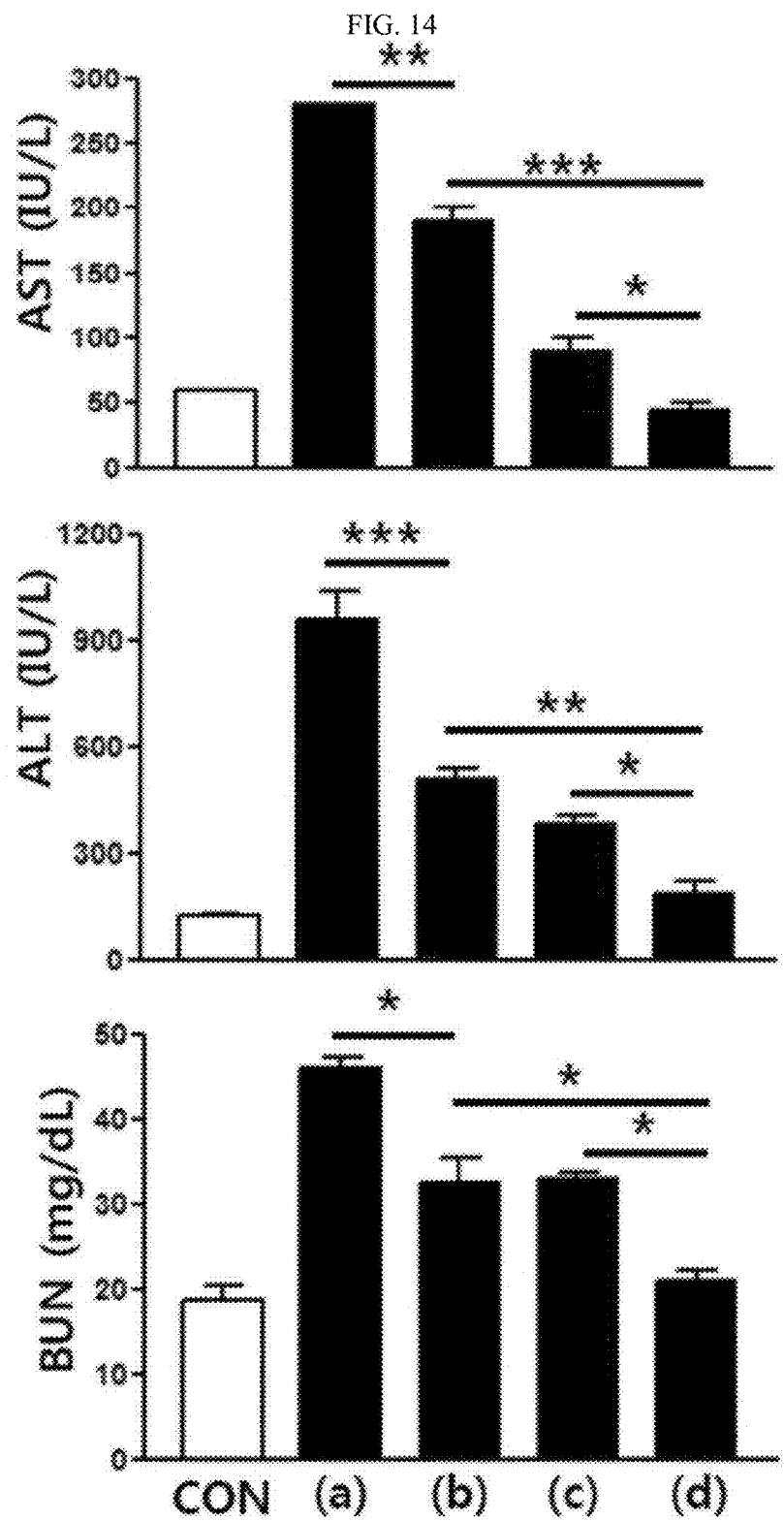
FIG. 14 is a diagram showing the concentrations of AST, ALT and BUN in serum when the ADK protein or an antibiotic (gentamicin) was administered to a sepsis animal model.

In addition, as shown in FIG. 14, it was confirmed that concentrations of AST, ALT and BUN in sera, known to be associated with liver and kidney toxicity, in the negative control (CON) were increased by sepsis, and when the mouse ADK protein was administered in combination with gentamicin, the markers were significantly decreased, and there was a significant difference from the single treatment group.

Figure 15:
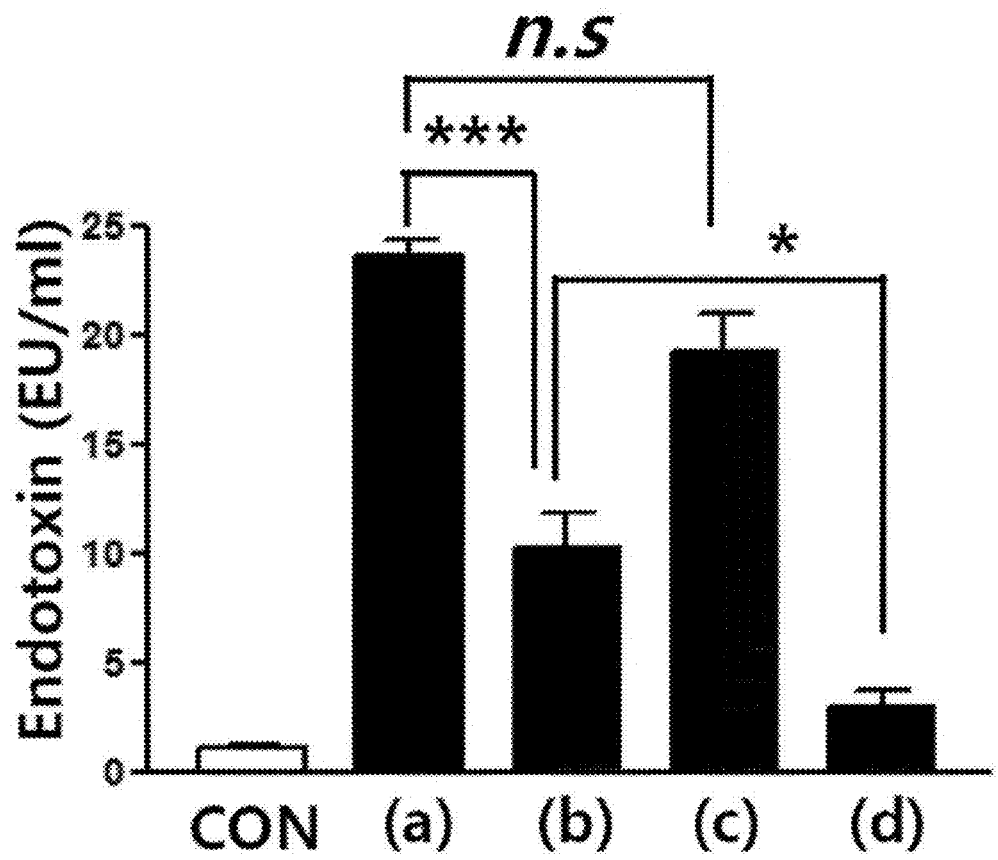
FIG. 15 is a diagram showing the amount of endotoxins in serum when the ADK protein or an antibiotic (gentamicin) is administered to a sepsis animal model.

In addition, as shown in FIG. 15, it was confirmed that, when the ADK protein was administered in combination with gentamicin, the amount of endotoxins in mouse sera, which was increased by sepsis, was significantly decreased. However, in a gentamicin-only group, a significant difference from the negative control (CON) was not observed, and therefore, it was confirmed that the antibiotic, gentamicin, was not able to eliminate endotoxins isolated from dead bacteria and had side effects in that the gentamicin-only group did not take action against a secondary infection, and when the ADK protein was administered in combination, the side effects caused by the antibiotic were able to be minimized.

6-3. Tissue Analysis

Twelve hours after sepsis induction, lung and spleen tissues were extracted from each mouse, prepared into paraffin sections according to a conventionally known method, and stained by H&E staining, followed by observation using a microscope. Results are shown in FIGS. 16 and 17.

Figure 16:
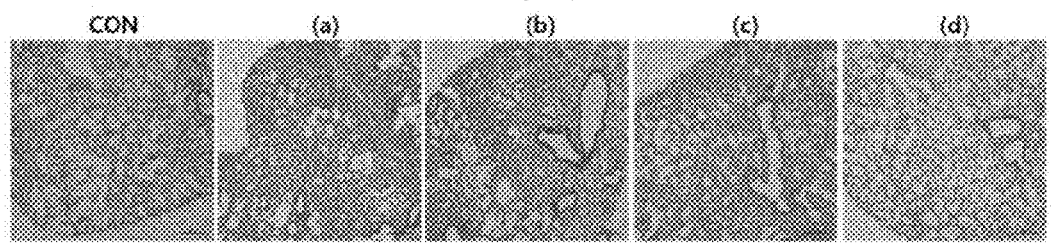
FIG. 16 is a diagram showing a degree of infiltration of inflammation-causing cells in lung tissue when the ADK protein or an antibiotic (gentamicin) is administered in a sepsis animal model.

As shown in FIG. 16, when the ADK protein was administered in combination with gentamicin, it was confirmed that infiltration of inflammation-induced cells was significantly reduced in the lung tissue, compared to the negative control (CON) and the single treatment group.

Figure 17:
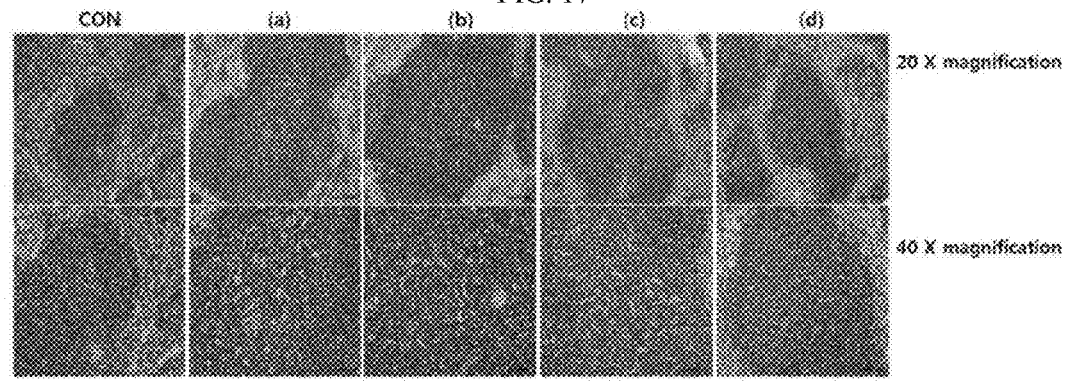
FIG. 17 is a diagram showing a degree of apoptosis in spleen tissue when the ADK protein or an antibiotic (gentamicin) is administered in a sepsis animal model.

In addition, as shown in FIG. 17, when the ADK protein was administered in combination with gentamicin, it was confirmed that apoptosis was significantly reduced in spleen tissue, compared to the negative control (CON) and the single treatment group.

6-4. Analysis of Apoptosis of B and T Cells in Spleen Cells

Twelve hours after sepsis induction, spleen cells were isolated from each mouse, apoptosis of B and T cells was analyzed using flow cytometry (FACS analysis) according to a conventionally known method (using FITC-conjugated Annexin V staining). A result is shown in FIG. 18.

Figure 18:
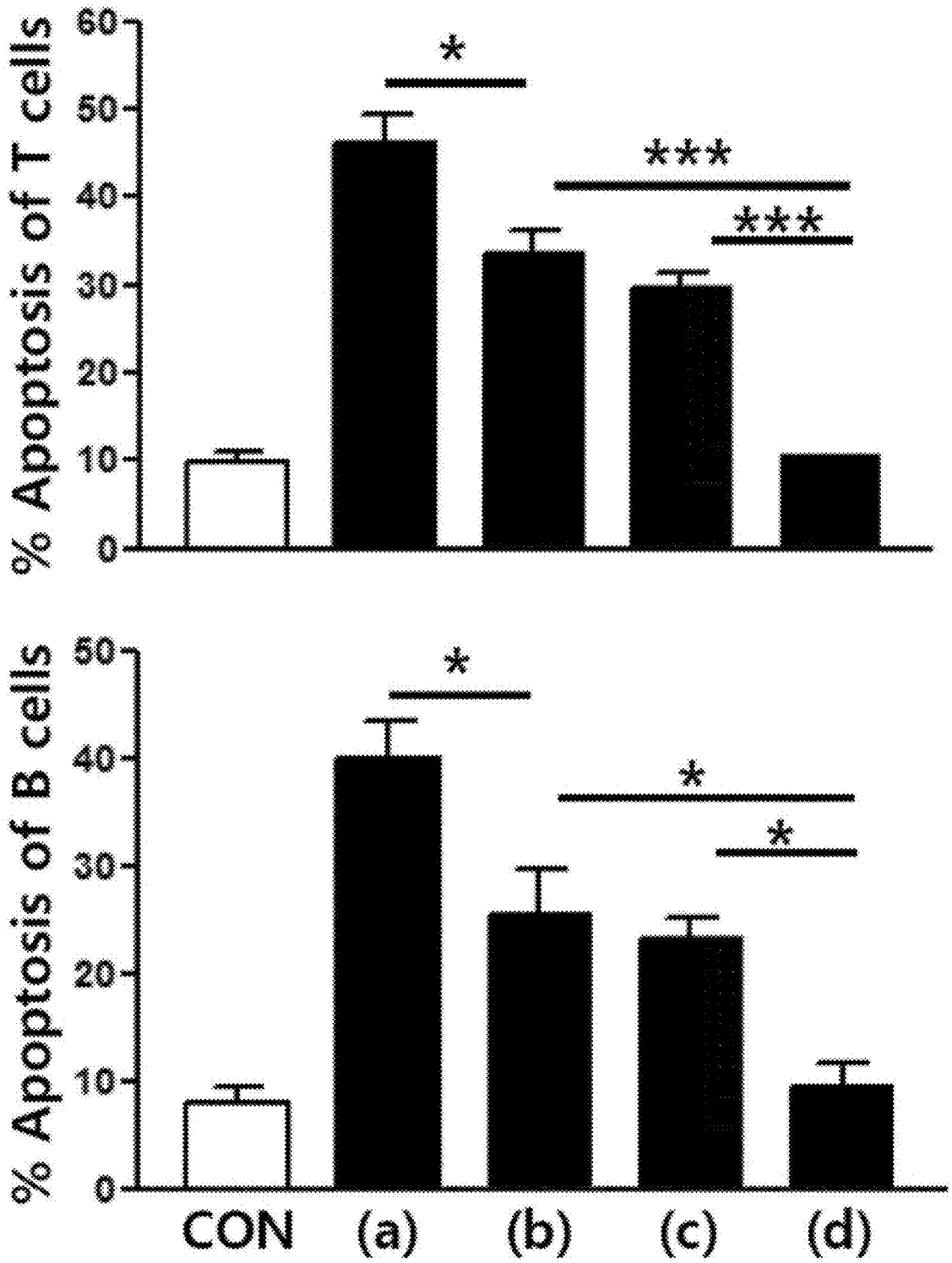
FIG. 18 is a diagram showing degrees of apoptosis of B cells and T cells in spleen cells when the ADK protein or an antibiotic (gentamicin) is administered in a sepsis animal model.

As shown in FIG. 18, it was confirmed that the apoptosis of B and T cells increased by sepsis in the negative control (CON) was significantly reduced when the ADK protein was administered in combination with gentamicin, and had a significant difference from the single treatment group.

6-5. Analysis of Number of Bacteria in Each Tissue

Twelve hours after sepsis induction, the liver, lungs and kidney were extracted from each mouse, and each tissue was disrupted in a PBS solution using a bullet blender homogenizer (Next Advance, N.Y., USA). Afterward, a supernatant was plated on a LB agar plate and incubated at 37° C., followed by analyzing whether bacteria were removed from each tissue. A result is shown in FIG. 19.

Figure 19:
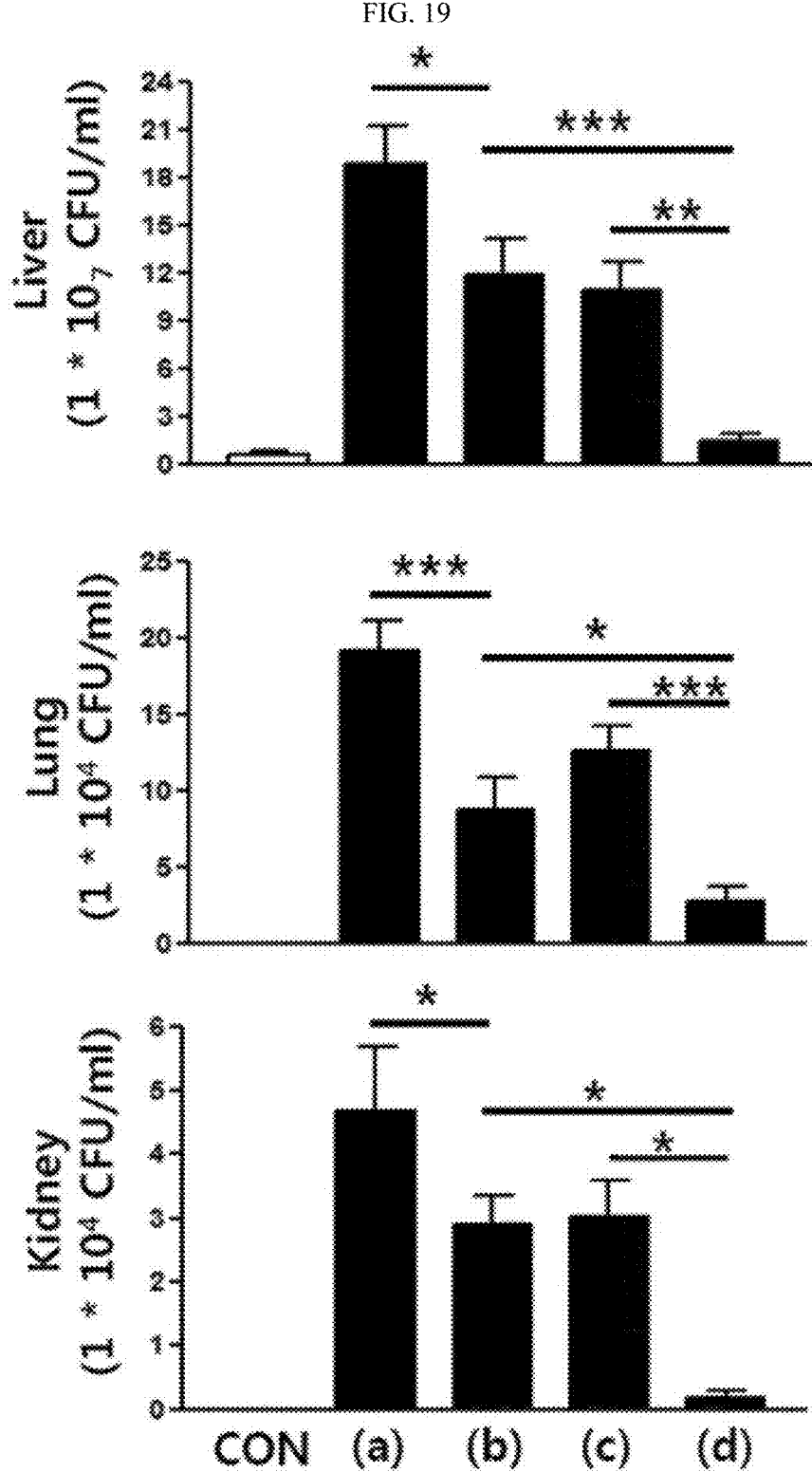
FIG. 19 is a diagram showing degrees of eliminating bacteria in liver, lung and kidney tissues when the ADK protein or an antibiotic (gentamicin) is administered in a sepsis animal model.

As shown in FIG. 19, when the ADK protein was administered in combination with gentamicin, it was confirmed that bacterial removal was significantly increased from liver, lung and kidney tissues, compared to the negative control (CON) and the single treatment group.

From the above-described experimental results, it was confirmed that, since the ADK protein has an excellent effect of eliminating endotoxins isolated from dead bacteria as well as inhibiting bacterial proliferation, unlike the antibiotics known up to now, when administered in combination with an antibiotic, the ADK protein can minimize side effects caused by the antibiotic, and exhibit a significantly excellent sepsis treatment effect, compared to the single administration.

Hereinafter, preparation examples of the pharmaceutical composition and the food composition of the present invention will be described to merely explain the present invention in detail, not to limit the present invention.

Preparation Example 1. Preparation of Pharmaceutical Composition 1-1. Preparation of Powder Product
2 g of ADK protein
1 g of Lactose The above components were mixed, and then the mixture was placed in an air-tight container, thereby preparing a powder product.

1-2. Preparation of Tablets 100 mg of ADK protein 100 mg of Corn starch 100 mg of Lactose 2 mg of Magnesium stearate The above components were mixed, and compressed to make a tablet product according to a conventional method for preparing a tablet.

1-3. Preparation of Capsules 100 mg of ADK protein 100 mg of Corn starch 100 mg of Lactose 2 mg of Magnesium stearate The above components were mixed, the mixture was contained in a gelatin capsule to make a capsule product according to a conventional method for preparing a capsule.

Preparation Example 2. Preparation of Food Composition 2-1. Preparation of Health Food 100 mg of ADK protein Vitamin mixture q.s.

70 g of Vitamin A acetate 1.0 mg of Vitamin E 0.13 mg of Vitamin B1

0.15 mg of Vitamin B2

0.5 mg of Vitamin B6

0.2 g of Vitamin B12

10 mg of Vitamin C 10 g of Biotin 1.7 mg of Nicotinamide 50 g of Folic acid 0.5 mg of Calcium pantothenate Mineral mixture q.s.

1.75 mg of Ferrous sulfate 0.82 mg of Zinc oxide 25.3 mg of Magnesium carbonate 15 mg of Potassium phosphate, monobasic 55 mg of Potassium phosphate, dibasic 90 mg of Potassium citrate 100 mg of Calcium carbonate 24.8 mg of Magnesium chloride Although the composition ratios of the vitamin and the mineral mixtures were prepared by mixing components relatively suitable for health food according to an exemplary embodiment, the mixing ratio may be randomly changed. The components may be mixed according to a conventional method for preparing health food to prepare granules, and may be used to prepare a health food composition according to a conventional method.

The invention claimed is:

1. A method for preventing, improving or treating an infectious disease caused by gram-negative bacteria, comprising administering to a subject in need thereof a composition comprising an effective amount of an adenylate kinase (ADK) protein.

2. The method of claim 1, wherein the gram-negative bacteria are one or more species selected from the group consisting of *Escherichia, Pseudomonas, Acinetobacter, Salmonella, Klebsiella, Neisseria, Enterobacter, Shigella, Moraxella, Helicobacter, Stenotrophomonas, Bdellovibrio* and *Legionella* genera.

3. The method of claim 1, wherein the gram-negative bacteria are one or more selected from the group consisting of *Escherichia coli, Pseudomonas aeruginosa, Pseudomonas fluorescens, Pseudomonas putida, Pseudomonas chlororaphis, Pseudomonas pertucinogena, Pseudomonas stutzeri, Pseudomonas syringae, Acinetobacter baumannii, Acinetobacter lwoffii, Acinetobacter calcoaceticus, Acinetobacter haemolyticus, Salmonella enterica, Salmonella bongori, Salmonella enteritidis, Salmonella typhimurium, Salmonella gallinarum, Salmonella pullorum, Salmonella mbandaka, Salmonella choleraesuis, Salmonella thompson, Salmonella infantis, Salmonella derby, Klebsiella pneumoniae, Klebsiella granulomatis, Klebsiella oxytoca, Klebsiella terrigena, Neisseria gonorrhoeae, Neisseria meningitidis, Enterobacter aerogenes, Enterobacter cloacae, Shigella boydii, Shigella dysenteriae, Shigella flexneri, Shigella sonnei, Moraxella catarrhalis, Moraxella lacunata, Moraxella bovis, Helicobacter pylori, Helicobacter heilmannii, Helicobacter fells, Helicobacter mustelae, Helicobacter fennelliae, Helicobacter rappini, Helicobacter hepaticus, Helicobacter bilis, Helicobacter pullorum, Stenotrophomonas maltophilia, Stenotrophomonas nitritireducens, Bdellovibrio bacteriovorus, Legionella pneumophila, Legionella anisa, Legionella birminghamensis, Legionella bozemanii, Legionella cincinnatiensis, Legionella dumoffii, Legionella feeleii, Legionella gormanii, Legionella hackeliae, Legionella israelensis, Legionella jordanis, Legionella lansingensis, Legionella longbeachae, Legionella maceachernii, Legionella micdadei, Legionella oakridgensis, Legionella sainthelensi, Legionella tucsonensis*, and *Legionella wadsworthii*.

4. The method of claim 1, wherein the composition is an antibacterial food composition, pharmaceutical composition, food addition composition, or feed additive composition.

5. A method for preventing, improving or treating sepsis or septic shock, caused by gram-negative bacteria, comprising administering to a subject in need thereof a composition comprising an effective amount of an adenylate kinase (ADK) protein and an antibiotic.

6. The method of claim 5, wherein the antibiotic is one or more selected from the group consisting of an aminoglycoside-, penicillin-, cephalosporin-, tetracycline-, macrolide-, streptogramin-, glycopeptide-, peptide-, flavophospholipol-, polyether-, phenicol-, lincosamide-, rifamycin-, polyene-, sulfonamide-, benzylpyrimidine-, quinolone-, fluoroquinolone- and nitrofuran-based antibiotic.

7. The method of claim 6, wherein the aminoglycoside-based antibiotic is one or more selected from the group consisting of gentamicin, kanamycin, ribostamycin, tobramycin, sisomicin, astromicin, isepamicin, arbekacin, dibekacin, spectinomycin, netilmicin, micronomycin, streptomycin, dihydrostreptomycin, apramycin, destomycin, hygromycin, amikacin, and neomycin.

8. The method of claim 5, wherein the composition is a food composition, pharmaceutical composition, food additive composition, or feed additive composition.

9. The method of claim 1, wherein the ADK protein is derived from *Mycobacterium tuberculosis*.

10. The method of claim 1, wherein the ADK protein is represented by SEQ ID NO: 1.

11. The method of claim 1, wherein the ADK protein is encoded by a nucleic acid sequence represented by SEQ ID NO: 2.

12. The method of claim 5, wherein the ADK protein is derived from *Mycobacterium tuberculosis*.

13. The method of claim 5, wherein the ADK protein is represented by SEQ ID NO: 1.

14. The method of claim 5, wherein the ADK protein is represented by SEQ ID NO: 1.

* * * * *

SEQUENCE LISTING

<160> NUMBER OF SEQ ID NOS: 2

<210> SEQ ID NO 1
<211> LENGTH: 181
<212> TYPE: PRT
<213> ORGANISM: Mycobacterium tuberculosis

<400> SEQUENCE: 1

```
Met Arg Val Leu Leu Leu Gly Pro Pro Gly Ala Gly Lys Gly Thr Gln
 1               5                  10                  15

Ala Val Lys Leu Ala Glu Lys Leu Gly Ile Pro Gln Ile Ser Thr Gly
            20                  25                  30

Glu Leu Phe Arg Arg Asn Ile Glu Gly Thr Lys Leu Gly Val Glu
        35                  40                  45

Ala Lys Arg Tyr Leu Asp Ala Gly Asp Leu Val Pro Ser Asp Leu Thr
    50                  55                  60

Asn Glu Leu Val Asp Asp Arg Leu Asn Asn Pro Asp Ala Ala Asn Gly
65                  70                  75                  80

Phe Ile Leu Asp Gly Tyr Pro Arg Ser Val Glu Gln Ala Lys Ala Leu
                85                  90                  95

His Glu Met Leu Glu Arg Arg Gly Thr Asp Ile Asp Ala Val Leu Glu
            100                 105                 110

Phe Arg Val Ser Glu Glu Val Leu Leu Glu Arg Leu Lys Gly Arg Gly
        115                 120                 125

Arg Ala Asp Asp Thr Asp Asp Val Ile Leu Asn Arg Met Lys Val Tyr
130                 135                 140

Arg Asp Glu Thr Ala Pro Leu Leu Glu Tyr Tyr Arg Asp Gln Leu Lys
145                 150                 155                 160

Thr Val Asp Ala Val Gly Thr Met Asp Glu Val Phe Ala Arg Ala Leu
                165                 170                 175

Arg Ala Leu Gly Lys
            180
```

<210> SEQ ID NO 2
<211> LENGTH: 546
<212> TYPE: DNA
<213> ORGANISM: Mycobacterium tuberculosis

<400> SEQUENCE: 2

```
gtgagagttt tgttgctggg accgcccggg gcgggcaagg ggacgcaggc ggtgaagctg     60
gccgagaagc tcgggatccc gcagatctcc accggcgaac tcttccggcg caacatcgaa    120
gagggcacca agctcggcgt ggaagccaaa cgctacttgg atgccggtga cttggtgccg    180
tccgacttga ccaatgaact cgtcgacgac cggctgaaca atccggacgc ggccaacgga    240
ttcatcttgg atggctatcc acgctcggtc gagcaggcca aggcgcttca cgagatgctc    300
gaacgccggg ggaccgacat cgacgcggtg ctggagtttc gtgtgtccga ggaggtgttg    360
ttggagcgac tcaaggggcg tggccgcgcc gacgacaccg acgacgtcat cctcaaccgg    420
atgaaggtct accgcgacga gaccgcgccg ctgctggagt actaccgcga ccaattgaag    480
accgtcgacg ccgtcggcac catggacgag gtgttcgccc gtgcgttgcg ggctctggga    540
aagtag                                                              546
```